US011026906B2

(12) United States Patent
Nelson

(10) Patent No.: US 11,026,906 B2
(45) Date of Patent: Jun. 8, 2021

(54) PHARMACEUTICAL QUALITY STRONTIUM L-LACTATE

(71) Applicant: Deanna J. Nelson, Raleigh, NC (US)

(72) Inventor: Deanna J. Nelson, Raleigh, NC (US)

(*) Notice: Subject to any disclaimer, the term of this patent is extended or adjusted under 35 U.S.C. 154(b) by 0 days.

(21) Appl. No.: 16/580,551

(22) Filed: Sep. 24, 2019

(65) Prior Publication Data

US 2020/0016101 A1 Jan. 16, 2020

Related U.S. Application Data

(63) Continuation of application No. 15/715,814, filed on Sep. 26, 2017, now Pat. No. 10,463,636.

(60) Provisional application No. 62/402,120, filed on Sep. 30, 2016.

(51) Int. Cl.
| | | |
|---|---|---|
| *A61K 31/19* | (2006.01) | |
| *A61P 19/08* | (2006.01) | |
| *A61K 33/24* | (2019.01) | |
| *A61K 33/241* | (2019.01) | |

(52) U.S. Cl.
CPC .............. *A61K 31/19* (2013.01); *A61K 33/24* (2013.01); *A61K 33/241* (2019.01); *A61P 19/08* (2018.01); *A61K 2300/00* (2013.01)

(58) Field of Classification Search
CPC ........ C07C 53/122; A61K 31/19; A61K 33/24
See application file for complete search history.

(56) References Cited

U.S. PATENT DOCUMENTS

| | | | | |
|---|---|---|---|---|
| 4,056,567 | A * | 11/1977 | Lamberti | C07C 51/41 562/584 |
| 5,702,711 | A | 12/1997 | Parab | |
| 5,856,356 | A | 1/1999 | Tsouderos et al. | |
| 6,232,497 | B1 * | 5/2001 | Pischel | C07C 51/412 562/577 |
| 7,241,460 | B2 | 7/2007 | Jellum | |
| 7,589,235 | B2 | 9/2009 | Christgau et al. | |
| 7,595,342 | B2 | 9/2009 | Hansen et al. | |
| 8,183,409 | B2 | 5/2012 | Christgau et al. | |
| 8,541,471 | B2 | 9/2013 | Hansen et al. | |
| 8,609,616 | B2 | 12/2013 | Hansen et al. | |
| 8,623,422 | B2 | 1/2014 | Hansen et al. | |
| 2004/0214892 | A1 | 10/2004 | Krauskopf | |
| 2006/0122274 | A1 | 6/2006 | Hansen | |
| 2006/0216358 | A1 | 9/2006 | Hansen | |
| 2006/0275503 | A1 | 12/2006 | Hansen et al. | |
| 2007/0282127 | A1 * | 12/2007 | Christgau | C07C 51/412 562/524 |
| 2008/0090896 | A1 | 4/2008 | Brookler | |
| 2009/0137678 | A1 | 5/2009 | Christgau et al. | |
| 2011/0130370 | A1 | 6/2011 | Briault et al. | |
| 2011/0269675 | A1 | 11/2011 | Hansen | |
| 2013/0310573 | A1 * | 11/2013 | Divi | C07D 333/40 549/61 |

FOREIGN PATENT DOCUMENTS

| | | | |
|---|---|---|---|
| CN | 101117290 A | * | 2/2008 |
| WO | 2004/098618 | | 11/2004 |
| WO | 2005/082385 | | 9/2005 |
| WO | 2016/141219 | | 9/2016 |

OTHER PUBLICATIONS

Grisanti (Osteoporosis: Atoxic metal effect. Functional Medicine University Published online Feb. 9, 2014) (Year: 2014).*
Strontium hydroxide hexahydrate product page Sigma Aldrich (CAS RN 1311-10-0), (Year: 2020).*
Wood GB, et al. The Dispensatory of the United States of America. 190T J B Lippincott Co., Philadelphia, PA. pp. 1661-1662.
Speer JA, Hensley-Dunn ML.Strontianite composition and physical properties. Amer Minerol 1976; 61: 1001-1004.
D'Haese PC, et al. Increased bone strontium levels in hemodialysis patients with osteomalacia. Kidney Int. Mar. 2000; 57(3): 1107-14. PubMed PMID: 10720963.
Wheater G, et al. The clinical utility of bone marker measurements in osteoporosis. J Transl Med. Aug. 29, 2013; 11: 201. PubMed PMID: 23984630; PubMed Central PMCID: PMC3765909.
Saidak Z, Marie PJ. Strontium signaling: molecular mechanisms and therapeutic implications in osteoporosis. Pharmacol Ther. Nov. 2012; 136(2): 216-26. Epub Jul. 20, 202. PubMed PMID: 22820094.
Karsdal MA, et al. The coupling of bone and cartilage turnover in osteoarthritis: opportunities for bone antiresorptives and anabolics as potential treatments? Ann Rheum Dis. Feb. 2004; 73(2):336-48. Epub Nov. 27, 2013. PubMed PMID: 24285494.
Valdes AM, et al. Large scale meta-analysis of urinary C-terminal telopeptide, serum cartilage oligomeric protein and matrix metalloprotease degraded type II collagen and their role in prevalence, incidence and progression of osteoarthritis. Osteoarthritis Cartilage. May 2014; 22(5):683-9. Epub Feb. 25, 2014. PubMed PMID: 24576742.
Radojcic MR, et al. Biomarker of extracellular matrix remodelling C1M and proinflammatory cytokine interleukin 6 are related to synovitis and pain in end-stage knee osteoarthritis patients. Pain. Jul. 2017; 158(7):1254-1263. doi: 10.1097/j.pain.0000000000000908. PubMed PMID: 28333699.
Van Spil WE, et al. Serum and urinary biochemical markers for knee and hip-osteoarthritis: a systematic review applying the consensus BIPED criteria. Osteoarthritis Cartilage. May 2010; 18(5):605-12. Epub Feb. 6, 2010. PubMed PMID: 20175979.
Patra D, Sandell LJ. Recent advances in biomarkers in osteoarthritis. Curr Opin Rheumatol. Sep. 2011; 23(5):465-70. PubMed PMID: 21720244.
Dam EB, et al. Increased urinary excretion of C-telopeptides of type II collagen (CTX-II) predicts cartilage loss over 21 months by MRI Osteoarthritis Cartilage. Mar. 2009; 17(3):384-9. Epub Sep. 3, 2008. PubMed PMID: 18768336.
Querido W, et al. The effects of strontium on bone mineral: A review on current knowledge and microanalytical approaches. Micron. Jan. 2016;80:122-34. Epub Oct. 20, 2015. PubMed PMID: 26546967.

(Continued)

*Primary Examiner* — Theodore R. Howell
*Assistant Examiner* — George W Kosturko
(74) *Attorney, Agent, or Firm* — Casimir Jones S.C.; J. Mitchell Jones

(57) ABSTRACT

The present application relates to strontium L-lactate compositions and methods of use. The methods and compositions disclosed herein are particularly useful for providing bioavailable strontium to mammals and treating or preventing symptoms of bone and/or cartilage disorders.

10 Claims, 3 Drawing Sheets

(56) References Cited

OTHER PUBLICATIONS

De Melo Nunes R, et al. Strontium ranelate analgesia in arthritis models is associated to decreased cytokine release and opioid-dependent mechanisms. Inflamm Res. Oct. 2015; 64(10):781-7. Epub Aug. 6, 2015. PubMed PMID: 26245235.

Korgali E, et al. Effect of Strontium Chloride on Experimental Bladder Inflammation in Rat. Int Sch Res Notices. Oct. 29, 2014; 2014: 369292. ECollection 2014. PubMed PMID: 27355060; PubMed Central PMCID: PMC4897514.

Skoryna SC. Effects of oral supplementation with stable strontium. Canad Med Assn J Oct. 1, 1981; 125(7): 703-12.

McCaslin FE, Janes JM. Effects of stable strontium in treatment of osteoporosis. Chapter 33 (pp. 563-579) in Skoryna S. Handbook of Stable Strontium. Plenum Press, New York, 1981.

McCaslin FE, Janes JM. The effect of strontium lactate in the treatment of osteoporosis. Proc of the Staff Meetings of the Mayo Clinic, 34, 329-334, 1959.

Pan et al. "Strontium ranelate treatment in a postmenopausal woman with osteonecrosis of the jaw after long-term oral bisphosphonate administration: a case report" Clinical Interventions in Aging, 2017: 12 1089-1093.

Longato et al. "Osteonecrosis of the jaw in a patient with rheumatoid artritis treated with an oral aminobisphosphonate: a clinical case report" Clinical Cases in Mineral and Bone Metabolism 2013; 102(2): 139-141.

Fedele et al. "Up to a quarter of patients with osteonecrosis of the jaw associated with antiresorptive agents remain undiagnosed" British Journal of Oral and Maxillofacial Surgery 53 (2015) 13-17.

Stathopoulos et al. "Strontium ranelate improves delayed healing of osteolytic lesions of the jaw in a man with chronic osteomyelitis" Clinical Cases in Mineral and Bone Metabolism 2014; 11(1): 77-81.

International Search Report & Written Opinion, International Patent Application PCT/US2017/053434, dated Mar. 28, 2018.

Ros, J. et al. "Lactate Reduces Glutamate-Induced Neurotoxicity in Rat Cortex" Journal of Neuroscience Research 66:790-794 (2001).

Ling, B. et al. "D-Lactate altered mitochondrial energy production in rat brain and heart but not liver" Nutrition & Metabolism 2012, 9:6, pp. 1-8.

Gibbs, M. and L. Hertz "Inhibition of astrocytic energy metabolism by D-lactate exposure impairs memory" Neurochemistry International 52 (2008) 1012-1018.

Marcus, C.S. and F.W. Lengemann "Absorption of Ca45 and Sr85 from Solid and Liquid Food at Various Levels of the Alimentary Tract of the Rat", J. Nutrition, 77, 1962, pp. 155-160.

Kwatra, S. et al. "Alternative Routes of Drug Administration—Transdermal, Pulmonary & Parenteral" Indo Global Journal of Pharmaceutical Sciences, 2012, 2(4):409-426.

Chan, L. et al. "Neurocardiac Toxicity of Racemic D, L-Lactate Fluids" Integrative Physiological Behavioral Science, Oct.-Dec. 1994, vol. 29, No. 4, 383-394.

Huang, Yu-Shen et al. "Accumulation of methylglyoxal and D-lactate in Pb-induced nephrotoxicity in rats" Biomedical Chromatography. 2017; 31:e3869, pp. 1-10.

Karbouj, Rim "Aluminium leaching using chelating agents as compositions of food" Food and Chemical Toxicology 45 (2007) 1688-1693.

Milsom S, Ibbertson K, Hannan S, Shaw D, Pybus J. Simple test of intestinal calcium absorption measured by stable strontium. Brit Med J 1987; 295: 231-234.

McCaslin FE, Janes JM. Effects of stable strontium in treatment of osteoporosis. Chapter 33 in Skoryna SC. Handbook of Stable Strontium. Plenum Press: New York, 1981.

Krogsnaard K, Weis M, Christgau S. P342MO. A new strontium salt available in tablet form with improved bioavailability of strontium compared to strontium ranelate. Poster Abstracts. International Osteoporosis Foundation and National Osteoporosis Foundation 2006. Osteoporos Int (2006) 17(Suppl 2): 143. https://doi.org/10.1007/s00198-006-0097-y.

Evans L. Lactic acid. USP Monograph. U.S. Pharmacopeia, vol. 29, p. 1223. Official Jan. 1, 2007.

Anonymous. Digest of comments received on the Stimuli Article "General Chapter on Inorganic Impurities: Heavy Metals" Published in Pharmacopeial Forum 34(5); Apr. 22, 2009.

Karbouj K. Aluminium leaching using chelating agents as compositions of food. Food Chem Toxicol 2007; 45: 1688-1693.

Karton et al. D-Lactate and Metabolic Bone Disease in Patients Receiving Long-Term Parenteral Nutrition Journal of Parenteral and Enteral Nutrition 1989, vol. 13, No. 2, pp. 132-135.

Vieillard et al., Joint Bone Spine vol. 75 pp. 34-40, Published 2008.

Grisanti et al. Osteoporosis: A Toxic Metal Effect. Functional Medicine University published online Feb. 9, 2014.

Cori et al., J. Biol. Chem, vol. 81, pp. 389-403, Published 1929.

Longato et al. Clinical Cases in Mineral and Bone Metabolism vol. 10 pp. 139-141 Published 2013.

Proceedings from the American Pharmaceutical Association 40th Edition, published 1982 (pp. 895-896).

\* cited by examiner

PHARMACEUTICAL QUALITY STRONTIUM L-LACTATE

The present application is a continuation of U.S. patent application Ser. No. 15/715,814, filed Sep. 26, 2017, which claims priority to U.S. Provisional Patent Application No. 62/402,120, filed Sep. 30, 2016, each of which are incorporated by reference in their entireties.

BACKGROUND

Field of the Invention

The present application relates to pharmaceutical quality strontium L-lactate compositions and methods of use. The methods and compositions disclosed herein are particularly useful for providing bioavailable strontium to mammals and treating or preventing bone- and/or cartilage-related disorders.

Description of the Related Art

In the early 1900's, a number of strontium salts of unknown quality and purity were prepared and used medicinally. The "Dispensatory of the United States" (1907) states that strontium lactate, by way of example, was prepared in a step-wise process. [Wood G B, Remington J P, Sadtler S P. The Dispensatory of the United States of America, pp 1661-2. Philadelphia: J B Lippincott Co., 1907.] First, strontium nitrate was washed with ethanol before dissolution in water. Then dilute sulfuric acid was added in an attempt to precipitate barium sulfate and other insoluble metal sulfates and purify the strontium nitrate. After filtration to remove the precipitates, sodium carbonate was added to precipitate the strontium ion as strontium carbonate. After the strontium carbonate was isolated by filtration, it was added to a solution of lactic acid. After reaction was complete, a solution of strontium lactate was obtained. The product of these reactions, strontium lactate, often was not isolated, since strontium lactate is highly soluble in water and alcohols such as methanol and ethanol. Therefore, the aqueous solution containing the salt typically was diluted with glycerol to a known volume, and the diluted solutions were used medicinally. Alternatively, excess water was evaporated and strontium lactate trihydrate or strontium lactate anhydrous was isolated. Historical tests for quality and purity [as disclosed in the "Dispensatory of the United States" (1907) and corresponding "U.S. Pharmacopeias" (through 1955)] consisted of subjective observations about reactivity with acids and bases. Tests for quality and purity such as strontium analysis, HPLC analysis of lactate, HPLC analysis of organic impurities, determination of sterility and absence of endotoxins, were not performed.

More recent preparations of certain strontium salts are described in U.S. Patents and their foreign counterparts. U.S. Pat. Nos. 7,589,235, 7,595,342, 8,183,409, 8,541,471, 8,609,616, and 8,623,422 (assigned to Osteologix) disclose two general methods for the preparation of strontium salts—neutralization of an aqueous solution of an organic acid with strontium hydroxide or strontium carbonate (Eq. 1) and anion exchange between a water-soluble strontium salt and a water-soluble salt of an organic acid (Eq. 2).

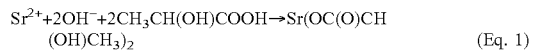
(Eq. 1)

(Eq. 2)

The acid-neutralization methods of preparation disclosed in U.S. Pat. No. 7,589,235 and related patents make use of high temperatures (e.g., 80-100° C.), optionally with elevated pressures, to accelerate the formation of strontium salts of organic acids in high yield and purity, where purity is defined as an absence of strontium carbonate contamination in the final product. The methods also disclose use of methanol or ethanol as a co-solvent said to cause precipitation of the strontium salt.

Historical medicinal uses of strontium salts included oral administration as an anthelmintic, antinephritic, diuretic, or tonic. Ingestion of daily doses of 0.3-0.6 grams of strontium lactate were reported to decrease albumin in the urine. Two gram doses twice a day for five days were reported as an effective treatment for worms. In addition, low doses effectively treated arthritis, gout, and involuntary movements (chorea).

Today several strontium salts, including strontium ranelate, strontium chloride, strontium succinate, strontium citrate, and strontium malonate, are reported to be useful for the treatment of bone and cartilage dysfunction, prevention of tooth decay, and prevention or treatment of pain. Two water-insoluble strontium salts, strontium ranelate and strontium succinate, have been approved as drugs for the treatment of osteoporosis in Europe and Australasia. Almost a decade of clinical use of a daily dose of 2 grams of strontium ranelate (680 mg strontium) supports a finding of significantly reduced incidence of fractures in men and women having low bone mass. Similar data gathered over a shorter period of time indicate a daily dose of 1.7 grams of strontium succinate (680 mg strontium) is also highly beneficial in treating osteoporosis. Other recent uses of strontium salts include preventing gastrointestinal side effects of a pharmaceutical product, treatment of rheumatic or arthritic conditions, and prevention or treatment of necrotic bone conditions. In U.S. Patent Application Publication No. US 2008/0090896 Brookler disclosed the use of strontium salts for the treatment of otosclerosis.

Moreover, recent studies have unexpectedly revealed that the strontium ion plays a more significant role in bone and cartilage maintenance than was known before the year 2000. Thus, recent studies suggest that when a water-insoluble strontium salt such as strontium ranelate or strontium succinate is administered orally as a treatment for osteoporosis, the strontium ion (the active ingredient) has an unexpected and unique mechanism of action mediated by a cation-sensing receptor (e.g., the calcium-sensing receptor), the receptor activator of nuclear factor kappa B (RANK)/RANK ligand (RANKL)/osteoprotegerin (OPG) pathway, and the fibroblast growth factor (FGF)/FGF receptor system. Strontium appears to beneficially increase pre-osteoblast proliferation, osteoblast differentiation, collagen type I synthesis, and bone matrix mineralization while inhibiting osteoclast differentiation and activation. This proposed dual mechanism of action has yielded significant positive effects on bone quality as assessed by diagnostic techniques such as high-resolution peripheral quantitative computed tomography (hr-pQCT) and microCT, as well as x-ray fluorescence (XRF). Both animal and human studies have shown that strontium is almost exclusively found in newly formed bone where it has been incorporated as apatite crystals. Higher levels of strontium are detected in cancellous than in cortical bone. Strontium is also reported to reduce the concentration and/or activity of inflammatory cytokines and mediators.

Of significance, studies of strontium ranelate showed that human exposure to therapeutic doses of the strontium ion does not cause gastric irritation, esophageal cancer, colon cancer, or osteonecrosis of the jaw—side effects which are common to other osteoporosis drug treatments that only slow osteoclast activity and bone resorption (such as bisphosphonates and desunomab).

All of the strontium salts in clinical use today (e.g., strontium ranelate, strontium succinate, strontium citrate, and strontium oxide) are water-insoluble strontium salts having a solubility in water of less than about 5 g/100 mL of water. None can be administered as solutions for injection. After ingestion, all require dissolution by stomach acid to release the strontium ion for uptake in the small intestine.

As a practical matter, however, most subjects using conventional water-insoluble strontium salts for the treatment of bone or joint disorders (such as osteoporosis or osteoarthritis, for example) are adults aged 40 or older who are afflicted with a variety of inflammatory metabolic disorders that adversely affect the gastrointestinal system. One example of the adverse effects of metabolic disorders on the gastrointestinal system is acid reflux. Individuals having acid reflux will consume over-the-counter treatments such as antacids (e.g., Pepcid), esomeprazole (e.g., NEXIUM) or omeprazole (e.g., PRILOSEC) to reduce stomach acidity from about pH 1 to about pH 5 and mitigate the acid reflux and inflammatory bowel disorders that many experience. As a result, water-insoluble treatments like strontium ranelate that require exposure to acidic gastric fluid for strontium release will be less effective. These water-insoluble salts will not dissolve extensively in the near neutral stomach fluids and will not release as much strontium ion as is needed for efficacy.

Thus, there is an unmet need for a water-soluble strontium salt (i.e., one having a solubility in water of greater than about 25 g/100 mL) that will release strontium ion in neutral solutions (e.g., solutions having a pH of 6-8). The present invention provides methods for the preparation and use of pharmaceutical quality strontium L-lactate compositions, a water-soluble strontium salt that meets these criteria and is expected to act both efficaciously and safely when used nutritionally or medicinally.

SUMMARY OF THE INVENTION

The present invention comprises nutritional and therapeutic, stable, pharmaceutical quality strontium L-lactate compositions that contain the strontium salt of L-lactic acid. Further, the compositions contain at most trace levels of metal contaminants such as aluminum, arsenic, barium, calcium, cadmium, chromium, lead, mercury, and thallium. The present invention also provides methods for the preparation of stable, pharmaceutical quality strontium L-lactate compositions, comprising (a) careful selection of raw materials of specified quality and purity; (b) reaction by neutralization of aqueous solutions of pharmaceutical quality L-lactic acid with pharmaceutical quality strontium carbonate, strontium hydroxide, or strontium oxide; or reaction by cation exchange between a water-soluble, pharmaceutical quality L-lactate salt and a water-soluble, pharmaceutical quality strontium salt; (c) careful control of reaction temperatures and reaction pH to prevent racemization of the L-lactate; and (d) isolation of the strontium L-lactate composition by precipitation under conditions which do not concentrate impurities into the precipitate. The methods comply with current Good Manufacturing Practices.

Accordingly, in some embodiments, the present invention provides methods of preparing a pharmaceutical quality strontium L-lactate composition comprising: a. selecting an L-lactic acid having at most trace concentrations of metals selected from the group consisting of aluminum, arsenic, barium, calcium, cadmium, chromium, lead, mercury, and thallium; b. selecting a strontium carbonate, strontium oxide, or strontium hydroxide having at most trace concentrations of metals selected from the group consisting of aluminum, arsenic, barium, calcium, cadmium, chromium, lead, mercury, and thallium; c. dissolving the L-lactic acid in water to obtain a homogeneous 0.1 M solution; d. adding portions of strontium carbonate, strontium oxide, or strontium hydroxide to the vessel containing the solution of L-lactic acid until a mass equal to 0.45-0.55 equivalents of L-lactic acid has been added and agitating the reaction mixture until a homogeneous solution is obtained; e. controlling the reaction temperature, solution pH, and reaction time to ranges sufficiently low to prevent racemization; f. removing particulate from the reaction mixture by filtration or centrifugation to provide a clarified solution; g. diluting the clarified solution with a sufficient volume of a water-miscible, aprotic organic solvent to form a precipitate; and h. isolating the precipitate and drying to constant mass to provide a pharmaceutical quality strontium L-lactate composition.

In some embodiments, the present invention provides methods of preparation of a pharmaceutical quality strontium L-lactate composition comprising: a. selecting a water-soluble salt of L-lactic acid having at most trace concentrations of metals selected from the group consisting of aluminum, arsenic, barium, calcium, cadmium, chromium, lead, mercury, and thallium; b. selecting a water-soluble strontium salt having at most trace concentrations of metals selected from the group consisting of aluminum, arsenic, barium, calcium, cadmium, chromium, lead, mercury, and thallium; c. dissolving one mole equivalent of the water-soluble L-lactate in the minimum volume of water needed to obtain a homogeneous solution; d. dissolving 0.45-0.55 mole equivalents of the water-soluble strontium salt in the minimum volume of water needed to obtain a homogeneous solution; e. adding the strontium salt solution to the vessel containing the L-lactate solution and agitating until a homogeneous solution is obtained; f. controlling the reaction temperature, solution pH, and reaction time to ranges sufficiently low to prevent racemization; h. removing particulate from the reaction mixture by filtration or centrifugation to provide a clarified solution; i. diluting the clarified solution with a sufficient volume of a water-miscible, aprotic organic solvent to form a precipitate; and j. isolating the precipitate and drying to constant mass to provide a pharmaceutical quality strontium L-lactate composition.

In some embodiments, the pharmaceutical quality strontium L-lactate composition made by the foregoing processes is characterized in having a strontium D-lactate content of less than about 3, 2 or 1 weight percent (i.e., weight strontium D-lactate per total weight of the pharmaceutical quality strontium L-lactate composition). In some embodiments, the pharmaceutical quality strontium L-lactate composition made by the foregoing processes is characterized in containing less than 100 ppm each of metals selected from the group consisting of aluminum, arsenic, barium, calcium, cadmium, chromium, lead, mercury, and thallium.

In some embodiments, the present invention provides a composition comprising an effective amount of a pharmaceutical quality strontium L-lactate composition. In some embodiments, the pharmaceutical quality strontium L-lactate composition is characterized in having a strontium D-lactate content of less than about 3, 2 or 1 weight percent. In some embodiments, the composition is characterized in containing less than 100 ppm each of metals selected from the group consisting of aluminum, arsenic, barium, calcium, cadmium, chromium, lead, mercury, and thallium. In some embodiments, the composition further comprises a pharmaceutically acceptable vehicle, carrier, or diluent. In some embodiments, the composition comprises a unit dose between about 10 mg to about 300 mg strontium.

In some embodiments, the present invention provides a composition comprising an effective amount of a pharmaceutical quality strontium L-lactate composition and a second active ingredient selected from the group consisting of calcium, calcium acetate, calcium citrate, calcium carbonate, calcium gluconate, calcium succinate, magnesium, magnesium ascorbate, magnesium acetate, magnesium citrate, vitamin K, glucosamine, chondroitin sulfate, and combinations thereof. In some embodiments, the pharmaceutical quality strontium L-lactate composition is characterized in having a strontium D-lactate content of less than about 3, 2 or 1 weight percent. In some embodiments, the composition is characterized in containing less than 100 ppm each of metals selected from the group consisting of aluminum, arsenic, barium, calcium, cadmium, chromium, lead, mercury, and thallium. In some embodiments, the composition comprises a unit dose between about 10 mg to about 300 mg strontium.

In some embodiments, the present invention provides methods of treating or preventing a disease, disorder, or condition associated with bone or cartilage dysfunction in a mammal known to have or be at risk for developing dysfunctional bone or cartilage, comprising administering an amount of a pharmaceutical quality strontium L-lactate composition effective to treat or prevent a disease, disorder, or condition associated with dysfunctional bone or cartilage maintenance in the mammal. Likewise, in some embodiments the present invention provides for use of an effective amount of a pharmaceutical quality strontium L-lactate composition to treat or prevent a disease, disorder, or condition associated with bone or cartilage dysfunction in a mammal known to have or be at risk for developing dysfunctional bone or cartilage. In some embodiments, the disease, disorder, or condition, is selected from the group consisting of dysregulations of bone metabolism, osteoporosis, osteopenia, osteoarthritis, osteopetrosis, Paget's disease, hypercalcemia of malignancy, myositis, periarticular erosions in rheumatoid arthritis, osteodystrophy, myositis issilicans, Bechterew's disease, malignant hypercalcemia, osteolytic lesions produced by bone metastasis, bone loss due to sex steroid hormone deficiency, bone abnormalities caused by cancer therapeutics, osteomalacia, Bechet's disease, hyperostosis, metastatic bone disease, immobilization-induced osteopenia or osteoporosis, osteoporosis pseudoglioma syndrome, idiopathic juvenile osteoporosis, bone necrosis caused by treatment with other therapeutic agents, osteonecrosis of the jaw, fracture healing after traumatic or atraumatic injury, or combinations of the foregoing. In some embodiments, the pharmaceutical quality strontium L-lactate composition is characterized in having a strontium D-lactate content of less than about 3, 2 or 1 weight percent. In some embodiments, the pharmaceutical quality strontium L-lactate composition is characterized in containing less than 100 ppm each of metals selected from the group consisting of aluminum, arsenic, barium, calcium, cadmium, chromium, lead, mercury, and thallium. In some embodiments, the amount of strontium L-lactate administered is between about 10 mg to about 2,000 mg strontium per day. In some embodiments, the strontium L-lactate is administered orally.

In some embodiments, the present invention provides methods of improving balance in bone remodeling comprising: identifying bone defects, reductions in bone strength, deterioration in bone architecture, or atypical progress in restoration of bone strength or architecture in a mammal; and administering a therapeutically effective amount of a pharmaceutical quality strontium L-lactate composition to the mammal. Likewise, in some embodiments, the present invention provides for use of an effective amount of a pharmaceutical quality strontium L-lactate composition to improve balance in bone remodeling in a subject with identified bone defects, reduction in bone strength, deterioration in bone architecture, or atypical progress in restoration of bone strength or architecture in a mammal. In some embodiments, the identifying includes administering a test that is sensitive to sensitive to detecting one of the following: bone defects, reductions in bone strength, deterioration in bone architecture, or atypical progress in restoration of bone strength or architecture. In some embodiments, the testing includes a diagnosis of one or more of bone defects, reductions in bone strength, deterioration in bone architecture, or atypical progress in restoration of bone strength or architecture. In some embodiments, the pharmaceutical quality strontium L-lactate composition is characterized in having a strontium D-lactate content of less than about 3, 2, or 1 weight percent. In some embodiments, the pharmaceutical quality strontium L-lactate composition is characterized in containing less than 100 ppm each of metals selected from the group consisting of aluminum, arsenic, barium, calcium, cadmium, chromium, lead, mercury, and thallium. In some embodiments, the amount of strontium L-lactate administered is between about 10 mg to about 2,000 mg strontium per day. In some embodiments, the strontium L-lactate is administered orally.

In some embodiments, the present invention provides methods of enhancing bone and hard tissue replacement comprising: identifying a need for bone or hard tissue replacement in a mammal; and administering a therapeutically effective amount of a pharmaceutical quality strontium L-lactate composition to the mammal. Likewise, in some embodiments, the present invention provides for use of an effective amount of a pharmaceutical quality strontium L-lactate composition to enhancing bone and hard tissue replacement in a mammal in need thereof. In some embodiments, the identifying includes administering a test that is sensitive to detecting or monitoring the progress of healing after bone or hard tissue replacement. In some embodiments, the testing includes a diagnosis of atypical progress in restoration of bone strength or architecture following replacement. In some embodiments, the pharmaceutical quality strontium L-lactate composition is characterized in having a strontium D-lactate content of less than about 3, 2, or 1 weight percent. In some embodiments, the pharmaceutical quality strontium L-lactate composition is characterized in containing less than 100 ppm each of metals selected from the group consisting of aluminum, arsenic, barium, calcium, cadmium, chromium, lead, mercury, and thallium. In some embodiments, the amount of strontium L-lactate administered is between about 10 mg to about 2,000 mg strontium per day. In some embodiments, the strontium L-lactate is administered orally.

In some embodiments, the present invention provides methods for preventing and treating bone pain comprising: identifying abnormal bone remodeling in a mammal that is associated with pain; and administering a therapeutically effective amount of strontium L-lactate to the mammal. Likewise, in some embodiments, the present invention provides for use of an effective amount of a pharmaceutical quality strontium L-lactate composition to prevent and/or treat bone pain in a mammal that has abnormal bone remodeling that is associated with pain. In some embodiments, the identifying includes administering a means of detecting abnormal bone remodeling that is associated with pain. In some embodiments, the testing includes a diagnosis of abnormal bone remodeling that is associated with pain. In some embodiments, the pharmaceutical quality strontium L-lactate composition is characterized in having a strontium D-lactate content of less than about 3, 2, or 1 weight percent. In some embodiments, the pharmaceutical quality strontium L-lactate composition is characterized in containing less than 100 ppm each of metals selected from the group consisting of aluminum, arsenic, barium, calcium, cadmium, chromium, lead, mercury, and thallium. In some embodiments, the amount of strontium L-lactate administered is between about 1 mg/kg body weight to about 100 mg/kg body weight strontium per day. In some embodiments, the strontium L-lactate is administered orally.

In some aspects, the compositions disclosed herein comprise an effective amount of a pharmaceutical quality strontium L-lactate composition and an effective amount of a second active ingredient such as calcium, calcium acetate, calcium citrate, calcium carbonate, calcium gluconate, calcium succinate, chondroitin preparations, glucosamine, magnesium, magnesium ascorbate, magnesium acetate, magnesium citrate, vitamin D, vitamin K, and combinations thereof.

In some aspects, the compositions disclosed herein may be used to treat or prevent a bone or joint disorder. For example, the compositions may be administered in order to restore deficiencies in bone strength and architecture caused by an imbalance in bone resorption and bone rebuilding or a deficiency in bone remodeling due to aging and/or the administration of one or more non-strontium containing drugs such as bisphosphonates or desunomab. The compositions may also be used to use treat or prevent diseases associated with defects in bone structure and architecture and/or associated with the damage related to defects in bone structure and architecture such as dysregulations of bone metabolism, osteoporosis, osteopenia, osteoarthritis, osteopetrosis, Paget's disease, hypercalcemia of malignancy, myositis, periarticular erosions in rheumatoid arthritis, osteodystrophy, myositis issilicans, Bechterew's disease, malignant hypercalcemia, osteolytic lesions produced by bone metastasis, bone loss due to sex steroid hormone deficiency, bone abnormalities caused by cancer therapeutics, osteomalacia, Bechet's disease, hyperostosis, metastatic bone disease, immobilization-induced osteopenia or osteoporosis, osteoporosis pseudoglioma syndrome, idiopathic juvenile osteoporosis, bone necrosis caused by treatment with other therapeutic agents, osteonecrosis of the jaw (ONJ), or fracture healing after traumatic or atraumatic injury, or combinations of the foregoing.

Some embodiments provide a method of preventing and treating bone pain.

Some embodiments provide a method of improving bone strength and architecture comprising: identifying a mammal with abnormal bone strength and architecture and administering a therapeutically effective amount of strontium L-lactate to the mammal. In some embodiments, the identifying includes administration of a test that is sensitive to detecting bone defects in strength and architecture such as assays for biomarkers of bone remodeling, analyses of tissue biopsies, and instrumental techniques such as high-resolution peripheral quantitative computed tomography (hr-pQCT) and microCT, as well as x-ray fluorescence (XRF). In some embodiments, the testing includes a diagnosis of decreased bone mass, deteriorating bone architecture, and bone defects contributing to increased risk of bone fracture.

Some embodiments provide a method of improving balance in bone remodeling in a mammal comprising: identifying abnormal bone resorption in a mammal; and administering a therapeutically effective amount of strontium L-lactate to the mammal to decrease the concentrations of biomarkers of resorption by osteoclasts to more normal ranges and increase the concentrations of biomarkers of bone rebuilding by osteoblasts to more normal ranges. In some embodiments, a method of improving balance in bone remodeling comprises administering a therapeutically effective amount of strontium L-lactate to the mammal to restore deficient bone remodeling by both osteoclasts and osteoblasts to more normal ranges.

Some embodiments provide a method of treating or preventing a disease, disorder, or condition associated with the bones of the inner ear in a mammal known to have or be at risk for developing tinnitus or hearing loss, comprising administering an amount of strontium L-lactate effective to treat or prevent a disease, disorder, or condition associated with bone dysfunction in the inner ear of a mammal.

Some embodiments provide a method of enhancing bone and hard tissue replacement comprising: identifying a need for bone or hard tissue replacement in a mammal; and administering a therapeutically effective amount of strontium L-lactate to the mammal. In some embodiments, the identifying includes administration of a test that is sensitive to detecting and/or monitoring the progress of the restoration of bone strength and architecture after bone or tissue replacement. Diagnostic techniques such as analyses of biomarkers, analyses of tissue biopsies, high-resolution peripheral quantitative computed tomography (hr-pQCT) and microCT, as well as x-ray fluorescence (XRF) are among the clinical tests that are useful for this purpose. In some embodiments, the therapeutically effective amount of the composition is administered in a cement or resin.

Some embodiments provide a method of treating or prophylaxis of a disease, disorder, or condition associated with cartilage dysfunction.

Some embodiments provide a method of treating or prophylaxis of a disease, disorder, or condition associated with an inflamed bowel.

Some embodiments provide a composition comprising an effective amount of strontium L-lactate and a pharmaceutically acceptable vehicle, carrier, or diluent. In some embodiments, the composition is a solid composition, including by way of example, tablets, capsules, sachets, powders, pellets, granules, granulates, and/or lozenges. In some embodiments, the composition comprises a sustained-release matrix. In some embodiments, the composition is enteric coated. In some embodiments, the composition is a liquid composition, including by way of example, solutions, syrups, suspensions, and/or emulsions.

In some embodiments, a unit dose of the composition comprises a mass of strontium L-lactate sufficient to provide between about 2 mg strontium per kilogram body weight of the subject to about 75 mg strontium per kilogram body weight of the subject. The unit dose is selected based in part on determination of the bioavailability of the strontium L-lactate composition in the subject and consideration of the average serum or synovial concentration of strontium that must be achieved to provide therapeutic benefit to the subject. In the absence of unit dosing information for a mammal other than humans, the unit dose that is administered will be about 2 mg per kilogram body weight and will increase until therapeutic benefit is observed. Diagnostic techniques such as high-resolution peripheral quantitative computed tomography (hr-pQCT) and microCT, as well as x-ray fluorescence (XRF) or analyses of tissue biopsies may be used to assess therapeutic benefit.

Optionally, the compositions are administered in a dosage regimen that includes administration of calcium, chondroitin preparations, glucosamine, vitamin D, and vitamin K.

Other features, advantages, and embodiments of the invention will be apparent to those of ordinary skill in the art from the following description, examples, and appended claims.

DETAILED DESCRIPTION OF THE INVENTION

Figure 1:
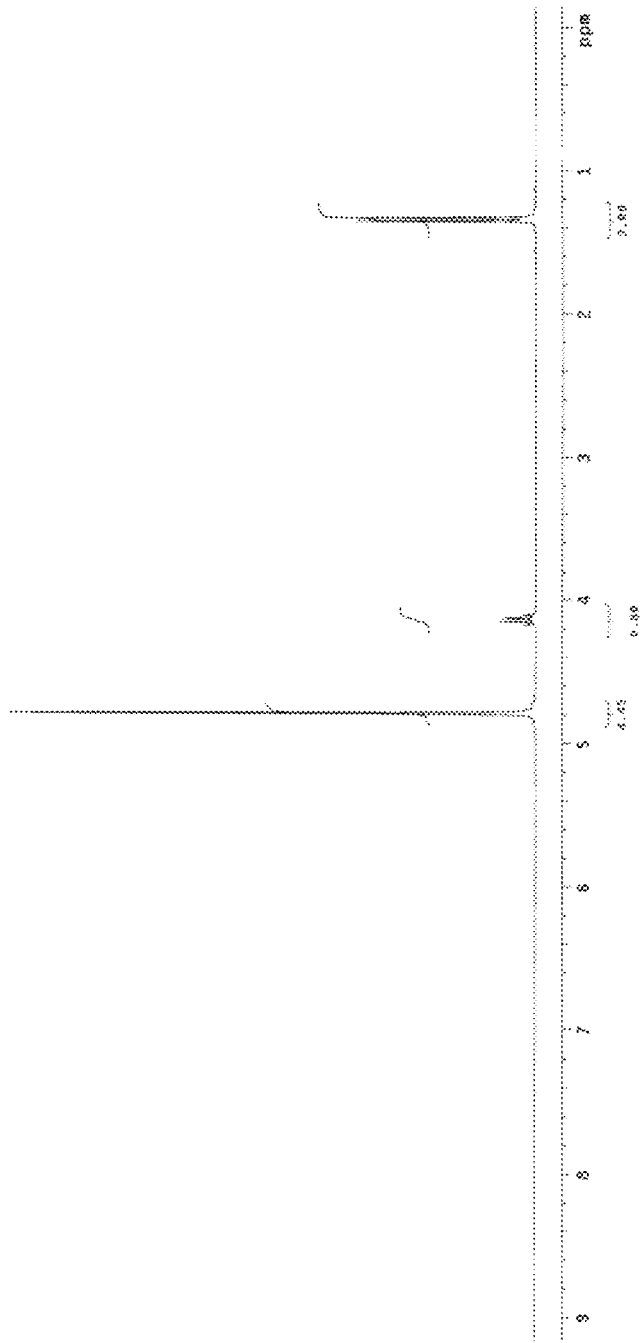
FIG. 1 is an NMR spectrum of strontium L-lactate of the invention as a solution in deuterium oxide ($D_2O$).

The terminology used in the description presented herein is not intended to be interpreted in any limited or restrictive manner, simply because it is being utilized in conjunction with a detailed description of certain specific embodiments described herein. Furthermore, embodiments described herein can include several novel features, no single one of which is solely responsible for its desirable attributes or which is essential to practicing the embodiments described herein.

As used herein, "identifying," refers to detecting or selecting a subject from a population of potential subjects, for example, to establish that a particular subject possesses certain properties or characteristics. "Identifying" may include, for example, self-identification, self-diagnosis, and diagnosis by a medical professional.

As used herein, the terms "preventing", "treating", "treatment", "prophylactic" and the like generally refer to obtaining a desired pharmacological and physiological effect. The terms "prophylactic treatment," "prevent," or "preventing," refers to treating a subject who does not yet exhibit symptoms of a disease or condition, but who is susceptible to, or otherwise at risk of, a particular disease or condition, whereby the treatment reduces the likelihood that the patient will develop the disease or condition. In addition, the effect may be prophylactic in terms of preventing or partially preventing a disease, symptom or condition thereof and/or may be therapeutic in terms of a partial or complete cure of a disease, condition, symptom or adverse effect attributed to the disease.

As used herein, a "disorder" is any condition that would benefit from treatment with the compositions described herein.

As used herein, a composition that "substantially" comprises a compound means that the composition contains more than about 98% by weight of the compound.

The term "about," unless otherwise stated explicitly herein, means±20%. For instance about 100 means 80 to 120, about 5 means 4 to 6, about 0.3 means 0.24 to 0.36, and about 60% means 48% to 72% (not 40% to 80%).

The term "pharmaceutical formulation" refers to preparations which, after administration, permit the biological activity of the active ingredients to be effective, and, therefore may be administered to a subject for therapeutic use.

A "therapeutically effective amount" as used herein includes within its meaning a sufficient amount of an active ingredient or composition comprising the same for use in the embodiments disclosed herein to provide the desired therapeutic effect in an acceptable relation to the risks associated with use of the active ingredient or composition. The exact amount of the active ingredient disclosed herein required will vary from subject to subject depending on factors such as the species being treated, the age and general condition of the subject, the severity of the condition being treated, the particular agent being administered, the weight of the subject, and the mode of administration and so forth. Thus, it is not possible to specify an exact "effective amount." However, for any given case, an appropriate "effective amount" may be determined by one of ordinary skill in the art using only routine methods. In some aspects, a therapeutically effective amount may include a dosing regimen.

In addition, the appropriate dosage of the compositions will depend, for example, on the condition to be treated, the severity and course of the condition, whether the composition is administered for preventive or therapeutic purposes, previous therapy, the patient's clinical history and response to the composition, the type of composition used, and the discretion of the attending physician. The composition is suitably administered to the patient at one time or over a series of treatments and may be administered to the patient at any time from diagnosis onwards. The composition may be administered as the sole treatment or in conjunction with other drugs or therapies useful in treating the condition in question.

As used herein, the term "strontium L-lactate" refers to the strontium salt of L-lactic acid, a salt having the general formula:

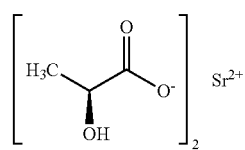

Strontium L-lactate is the strontium salt of the carboxylic acid L-lactic acid. Strontium L-lactate has a molecular weight of 265.8 g/mole. Its composition by weight is 37.4% Sr and 63.6% lactate. Some embodiments provide physiologically compatible strontium L-lactate hydrates, crystalline forms, polymorphic forms, solid forms having specific bulk densities or tap densities, and solid forms having specific particle sizes. Some embodiments provide compositions coated with pharmaceutically acceptable materials intended to modify its release and/or bioavailability, including, but not limited to Eudragit, microcrystalline cellulose, hydroxypropylmethylcellulose phthalate, and the like.

As used herein, the term "strontium" refers to the strontium ion, $Sr^{2+}$.

The term "L-lactate" means the anionic form of L-lactic acid, a monocarboxylic organic acid also known as sarcolactic acid; (S)-2-hydroxypropanoic acid; (S)-lactic acid;

(S)-2-hydroxypropionic acid; and L-(+)-lactic acid. L-Lactic Acid is the levorotatory isomer of lactic acid and is the biologically active isoform in humans. L-Lactic acid has Chemical Abstracts Service Registry No. 79-33-4, the molecular formula $C_3H_6O_3$, and the general formula:

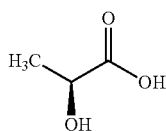

The term "pharmaceutical quality" as used herein refers to a substance that is manufactured in compliance with current Good Manufacturing Practices (cGMP). "Guidance for Industry—Quality Systems Approach to Pharmaceutical CGMP Regulations" provides a broad description of these regulations and requirements. ["Guidance for Industry—Quality Systems Approach to Pharmaceutical CGMP Regulations." U.S. Department of Health and Human Services, Food and Drug Administration, Center for Drug Evaluation and Research, Center for Biological Evaluation and Research, Center for Veterinary Medicine, Office of Regulatory Affairs, Rockville, Md. September 2008.] In addition, the term refers to a substance that is manufactured in compliance with current regulations relating to elemental impurities. "Guidance for Industry Q3D Elemental Impurities" provides a description of permitted daily exposure levels for elemental impurities in substances that are administered by mouth or by injection. ["Guidance for Industry—Q3D Elemental Impurities." U.S. Department of Health and Human Services, Food and Drug Administration, Center for Drug Evaluation and Research, Center for Biological Evaluation and Research, Rockville, Md. September 2015.]

The term "current Good Manufacturing Practices" refers to the requirements described in "Guidance for Industry, Q7A Good Manufacturing Practice Guidance for Active Pharmaceutical Ingredients," a publication of the U.S. Department of Health and Human Services, Food and Drug Administration, Center for Drug Evaluation and Research (CDER), Center for Biologics Evaluation and Research (CBER), Center for Veterinary Medicine, Office of Regulatory Affairs, Rockville, Md. September 2008. Compliance with requirements such as these satisfies a requirement for compliance with current Good Manufacturing Practices. The current version of this Guidance is incorporated by reference in its entirety.

The term "trace level" as used herein refers to the concentration of an element that is present in a substance. Acceptable trace levels will differ by element. In general, the term refers to a concentration of a metallic element other than strontium that is less than about 100 micrograms per gram of a substance. If a reagent, solvent, or reaction product meets this criterion, it is deemed pharmaceutically acceptable as indicated by the acronym "PA"

As used herein, the term "pharmaceutically acceptable solvent" means water, water for injection, aqueous buffer solutions that are physiologically compatible, as well as aqueous solutions containing organic solvents that are physiologically compatible. A non-comprehensive list of pharmaceutically acceptable solvents is provided in U.S. Department of Health & Human Services, Food & Drug Administration, "Guidance for Industry: Q3C Impurities: Residual Solvents," September 2006 or its current issue.

As used herein, the terms "calcium" and "magnesium" refer to the calcium ion $Ca^{2+}$ and the magnesium ion $Mg^{2+}$, respectively.

As used herein, the term "bioavailability" refers to the amount of a substance that is absorbed in the intestines and ultimately available for biological activity in a subject's tissues and cells.

As used herein, the term "enhancing the bioavailability" and the like are used herein to refer to obtaining a desired pharmacological and physiological effect by increasing the amount of strontium that is absorbed from the intestine or is taken up by target tissues and cells after administration of a composition to a mammal.

As used herein, the term "therapeutically effective" is intended to qualify the amounts of a strontium L-lactate composition which will achieve the goal of providing the quantity of strontium needed to prevent and treat adverse effects associated with bone and/or cartilage disorders or reducing the quantity and/or activity of inflammatory mediators such as cytokines and matrix metalloproteinases. The amounts of a strontium L-lactate composition may be administered orally to a subject as part of the same unit dose or as different unit doses administered in a coordinated manner. Further, the amounts of a strontium L-lactate composition may be administered in a coordinated manner by different routes of administration, if required to ensure bioavailability in a subject requiring this treatment. By way of example, administration in a coordinated manner may comprise administration of an effective amount of a strontium L-lactate by oral, topical, or intravenous administration at a time point and oral administration of an effective amount of a strontium L-lactate composition at a separate time point within 72 hours of administration of the first effective amount of said composition.

As used herein, the term "excipient material" refers to any compound that is part of a formulation that is not an active ingredient, i.e., one that has no relevant biological activity, and which is added to the formulation to provide specific characteristics to the dosage form, including by way of example, providing protection to the active ingredient from chemical degradation, facilitating release of a tablet or caplet from equipment in which it is formed, and so forth.

"Balance in bone remodeling" means that the actions of bone resorption by osteoclasts and bone deposition by osteoblasts are coupled to achieve a restoration of bone strength, mass and architecture to values expected for a mammal of a specific age and sex. Moreover, the terminology means that these two functions are tightly coupled not only quantitatively, but also in time and space. It is known that when the coupling is lost, the correct bone mass and architecture could be compromised, leading to several skeletal pathologies such as microfractures or fractures.

As used herein, the term "bone quality" refers to the combination of structural and material parameters that collectively enable bone to bear load and resist fracture or excessive deformation. Bone quality may be evaluated using clinical diagnostic techniques such as analyses of tissue biopsies, assays for biomarkers of bone remodeling, high-resolution peripheral quantitative computed tomography (hr-pQCT) and microCT, as well as x-ray fluorescence (XRF).

For the purpose of this disclosure, a warm-blooded animal is a member of the animal kingdom which includes but is not limited to mammals and birds. The most preferred mammal of this application is human.

To provide a more concise description, some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the experimental and/or measurement conditions for such given value.

In the description of the invention that follows the composition is described as the percentage by weight of each ingredient relative to the weight of the complete composition. Thus, a text which reads "10% Y" means that the amount of the ingredient Y was 10 percent by weight relative to the weight of the total composition.

Methods for the preparation of a strontium L-lactate composition of the invention comprise the following.

A. Requirements for a Pharmaceutical Quality Strontium L-Lactate.

The invention requires strontium salt of L-lactate having pharmaceutical quality. Conventional preparations of strontium lactate cannot be classified as pharmaceutical quality strontium L-lactate. The carboxylate anion lactate has two enantiomeric forms—L-lactate and D-lactate. A 1:1 mixture of these enantiomers is known as DL-lactate and has no optical rotation. L-Lactate is the form found in nature, and a solution of its sodium salt has an optical rotation of −13.5° (c=2.5 in 1.5 M NaOH at 20° C.). D-Lactate has an optical rotation of +13.5° under the same conditions. DL-Lactate is a synthetic composition made up of equal parts D- and L-lactate (i.e., a racemic mixture) and has no optical rotation. Published methods for the preparation of strontium lactate do not specify whether the strontium salt is the L-lactate salt, the D-lactate salt, or the DL-lactate salt. The physical and chemical properties of each of these compositions are expected to differ from one salt to another. [See, by way of example, the differences in the properties of lactic acid that are summarized in http://en.wikipedia.org/wiki/Lactic_acid, as well as the discussion of Bancroft and Davis, J. Phys. Chem., 35: 2508 (1931).]

This distinction is also significant because D-lactate, whether administered as the single isomer or as part of a racemic D,L-lactate mixture, causes toxicity. Blood concentrations of D-lactate of 3 mmol/L or greater cause acidosis and variably presenting encephalopathies. Symptoms of toxicity may include memory loss, fatigue, changes in personality, changes in speech, gait, or balance, panic reaction, or cerebellar symptoms such as ataxia or dysarthria. Severe cases may involve syncope, coma, serious disturbances in heart rate and rhythm, and respiratory failure. People who have diabetes, vitamin B deficiencies, or renal failure and those who have undergone gastric bypass or bowel surgery are at high risk for D-lactate-related toxicities.

Likewise, the invention essentially requires that a pharmaceutical quality strontium L-lactate composition be free of toxic metal contaminants. Since the early 1900's the need for reduction in the concentrations of heavy metal contaminants (e.g., arsenic, barium, cadmium, chromium, lead, or mercury) to low percentage levels has been recognized. Strontianite, one of the common raw materials used in manufacture of strontium lactate (vide infra), contains from about 6% to about 10% by weight calcium as well as barium and lead at the 2500-3600 ppm and the 100-600 ppm levels, respectively. [J. A. Speer and M. L. Hensley-Dunn. Strontianite composition and physical properties. Amer Minerol 1976; 61: 1001-1004.] Thus, conventional strontium lactate that is prepared using strontianite (natural form of strontium carbonate) may not meet this requirement for freedom from toxic metal contaminants. In addition, the pharmaceutical quality strontium L-lactate composition must have trace levels of concentrations of metal contaminants such as aluminum and thallium. Published reports indicate that this purity requirement has not been met by conventional strontium lactate. [See, by way of example, Schrooten et al. Kidney International, 54: 448 (1996) and D'Haese et al., ibid., 57: 1107 (2000).]

B. Ingredients:

The ingredients used in the preparation of compositions of the present invention are described here. Common ingredients such as water for injection or sodium hydroxide solution are not described.

PA Strontium Salt: A strontium salt is selected that contains at most trace levels of metal contaminants such as aluminum, arsenic, barium, calcium, cadmium, chromium, lead, mercury, and thallium. If the composition of the strontium salt is not provided by the manufacturer's certificate of analysis, the composition may be determined by graphite furnace atomic absorption spectroscopy (AAS) or inductively coupled plasma-mass spectrometry (ICP-MS). Strontium salts that do not meet this specification shall not be used in the preparation of pharmaceutical quality strontium L-lactate. The nitrate anion in strontium nitrate has potential physiological activity, and therefore, strontium nitrate is a less preferred raw material for the invention.

PA L-Lactate: L-Lactic acid or a water-soluble salt of L-lactic acid that contains at most trace levels of metal contaminants such as aluminum, arsenic, barium, cadmium, chromium, lead, mercury, and thallium is selected for use as a starting material for the preparation of pharmaceutical quality strontium L-lactate. If the composition of the L-lactate raw material is not provided by the manufacturer's certificate of analysis, the composition may be determined by graphite furnace atomic absorption spectroscopy (AAS) or inductively coupled plasma-mass spectrometry (ICP-MS). L-Lactates that do not meet this specification shall not be used in the preparation of pharmaceutical quality strontium L-lactate. Suitable water-soluble salts of L-lactic acid include, by way of example, the ammonium, sodium, trimethylammonium, triethylammonium, or N-methyl-glucamine salts of L-lactic acid. Because the potassium and lithium ions have potentially adverse physiological effects, potassium and lithium L-lactates are less preferred raw materials for preparation of a composition of the invention.

C. Compliance with current Good Manufacturing Practices (cGMP):

The raw materials, methods for the preparation and analysis, product compositions, and determinations of product composition stability shall comply with current Good Manufacturing Practices (cGMP). Compliance with the requirements described in "Guidance for Industry, Q7A Good Manufacturing Practice Guidance for Active Pharmaceutical Ingredients," a publication of the U.S. Department of Health and Human Services, Food and Drug Administration, Center for Drug Evaluation and Research (CDER), Center for Biologics Evaluation and Research (CBER), Rockville, Md., September 2008, satisfies this requirement. The current version of this Guidance is incorporated by reference in its entirety.

D. Processes for Preparation of a Strontium L-Lactate Composition of the Present Invention:

Preparation of a stable, pharmaceutical quality strontium L-lactate composition of the present invention employs conventional PA manufacturing equipment and conventional processing steps. In order to avoid oxidation, contamination, and/or degradation of the raw materials used in manufacturing, the use of glass-lined manufacturing vessels and an inert atmosphere is preferred. In order to maintain temperature control during manufacturing, the manufacturing vessels are equipped with external cooling systems in which recirculating coolant enables temperature control. In a process of the present invention, the following steps are employed. Each reagent is qualified for use in pharmaceutical manufacturing using written specifications that require the raw material to be pharmaceutically acceptable (PA). Each raw material that meets this requirement is then accurately weighed and/or volumetrically transferred into mixing vessels.

Steps in the preparation of pharmaceutical quality strontium L-lactate by neutralization of L-lactic acid (Method A).
1. Dissolution of L-lactic acid in water. L-Lactic acid is commercial available as a solid or as a 40% solution in water. Sufficient water is added to the solid or to the concentrate to obtain a 0.1 M solution. The solution is agitated until clear.
2. Strontium carbonate, strontium oxide, and strontium hydroxide are not soluble in water. The requisite mass of strontium carbonate, strontium oxide or strontium hydroxide is weighed. Portions are carefully added to the vessel containing L-lactic acid at a rate that a temperature of less than 60° C. was maintained, and agitation is continued until a clear solution is obtained. A total mass of strontium carbonate, strontium oxide, or strontium hydroxide equal to 0.45-0.55 equivalents of L-lactic acid is added.
3. After stirring for a period of time sufficient to allow complete reaction and dissipation of carbon dioxide (if strontium carbonate was used as the raw material), the clarity of the reaction mixture is determined. If the reaction mixture is cloudy, it is clarified by filtration or centrifugation.
4. The clarified reaction mixture is diluted with at least 6 volumes of an aprotic, water-miscible organic solvent (e.g., acetone, tetrahydrofuran, dimethylsulfoxide, and so forth). A white solid forms and is isolated by filtration and dried to constant mass. In this manner strontium L-lactate is obtained in at least about 90% yield.

Steps in the preparation of pharmaceutical quality strontium L-lactate by cation exchange of a water-soluble strontium salt with a water-soluble salt of L-lactic acid (Method B).
1. Dissolution of a water-soluble salt of L-lactic acid in water: A water-soluble salt of L-lactate acid is dissolved in the minimum volume of water needed to obtain a clear and colorless solution. The solution is agitated until clear.
2. Dissolution of a water-soluble strontium salt in water: A water-soluble strontium salt (e.g, strontium chloride) having a mass corresponding to 0.45-0.55 equivalents of the L-lactate in step 1 is dissolved in the minimum volume of water needed to obtain a clear and colorless solution. The solution is agitated until clear.
3. Portions of the second solution are carefully added to the vessel containing L-lactate and agitation is continued until a homogeneous solution is obtained.
4. The clarified reaction mixture is diluted with at least 6 volumes of an aprotic, water-miscible organic solvent (e.g., acetone, tetrahydrofuran, dimethylsulfoxide, and so forth). A white solid forms and is isolated by filtration and dried to constant mass. In this manner strontium L-lactate is obtained in at least about 70% yield.

The process may be readily scaled. Irrespective of whether Method A or Method B is employed for the preparation of the strontium L-lactate composition after scaling to commercial scales, both the temperature and the solution pH must be carefully controlled to prevent racemization of the L-lactate to D-lactate. (External cooling of the reaction vessel using a recirculating coolant accomplishes maintenance of temperatures less than about 60° C.) The risk of racemization is enhanced by exposure of the reaction solution to high temperatures (e.g., 80-100° C.) and high values of solution pH (e.g., pH>8) for extended periods of time. Thus, high temperatures and high values of solution pH for extended periods of time must be avoided.

In addition, both Method A and Method B require precipitation of the strontium L-lactate composition by dilution of the aqueous solution with an aprotic, water-miscible organic solvent. Dilution retains water-soluble contaminants in the aqueous phase and thus reduces the concentration of undesired contaminants in the precipitated product. By comparison, the conventional practice of solvent evaporation increases the concentration of undesired contaminants in the product, since all materials are concentrated to dryness. Thus, this step is a purification step as well as a step which separates the desired product from contaminating materials that remain in solution.

The preferred method of preparation of pharmaceutical quality strontium L-lactate is by reaction of an aqueous solution of PA L-lactic acid with PA strontium oxide. This method is preferred for reasons such as the following.

PA strontium oxide has only recently become commercially available as a consequence of its widespread use in the manufacture of electronics that requires strontium oxide of high purity. [Personal communication from a customer service representative at American Elements, Los Angeles, Calif.]

Under these conditions strontium oxide may be added in portions at a rate sufficient to allow careful temperature control by cooling. Temperature control prevents racemization of the L-lactate.

Under these conditions, the solution clarifies after each addition of strontium oxide, enabling monitoring of the course of the reaction. In contrast, addition of strontium carbonate to an aqueous solution of L-lactic acid causes the release of carbon dioxide, which forms bubbles and foam that dissipates very slowly. As the reaction nears completion, dissipation of the foam and gritty residue associated with it is so slow that heating is needed to clarify the solution. Heating increases the risk of racemization of the L-lactate. Likewise, if a solution of strontium hydroxide is prepared, the solution is so basic that it absorbs carbon dioxide from the atmosphere. Absorption of carbon dioxide creates a mixed strontium hydroxide-carbonate salt of uncertain proportions, solubility, and reactivity.

After completion of all of the steps in the method of preparation, pharmaceutical quality strontium L-lactate trihydrate is obtained. The product is characterized by its appearance as a mobile white powder, strontium content of about 27.4% by weight, L-lactate content of about 55.7% by weight, water content of about 16.9% by weight, concentrations of trace metals such as aluminum, arsenic, barium, cadmium, chromium, lead, mercury, and thallium of less than about 100 ppm of each metal, and an optical rotation (obtained as described in Example 6) of −9°+/−1°. The pharmaceutical quality strontium L-lactate trihydrate may be dried under vacuum to provide pharmaceutical quality strontium L-lactate anhydrous. (Drying of the solid trihydrate does not cause racemization.)

E. Compositions of the Invention:

Stable, pharmaceutical quality strontium L-lactate compositions are provided by the present invention. The methods of the invention yield strontium L-lactate•$3H_2O$ compositions. If the solid trihydrate is heated under vacuum to temperatures in the range from about 100° C. to about 130° C., the methods of the invention yield strontium L-lactate anhydrous compositions. No racemization is observed under these conditions.

The administration of one or more of the compositions disclosed herein can be by any of the methods of administration described herein or by delivery methods known by one of skill in the art. The compositions may be administered orally, through parenteral nutrition, e.g., feeding tube, intravenously, or topically, and through other known means.

For oral administration, the compositions disclosed herein can be provided as a tablet, aqueous or oil suspension, dispersible powder or granule, emulsion, hard or soft capsule, syrup, elixir, or beverage. Solid dosage forms such as tablets and capsules may comprise an enteric coating. Compositions intended for oral use can be prepared according to any method known in the art for the manufacture of pharmaceutically acceptable compositions and such compositions may include one or more of the following agents: sweeteners, flavoring agents, coloring agents, coatings, and preservatives. The sweetening and flavoring agents will increase the palatability of the preparation but will exclude artificial sweeteners known to increase the risk of cardiovascular dysfunction (e.g., aspartame). Tablets containing the complexes in admixture with non-toxic pharmaceutically acceptable excipients suitable for tablet manufacture are acceptable. Pharmaceutically acceptable vehicles such as excipients are compatible with the other ingredients of the formulation (as well as non-injurious to the patient). Such excipients include inert diluents such as calcium carbonate, sodium carbonate, lactose, calcium phosphate or sodium phosphate; granulating and disintegrating agents, such as corn starch or alginic acid; binding agents such as starch, gelatin or acacia; and lubricating agents such as magnesium stearate, stearic acid or talc. Tablets can be uncoated or can be coated by known techniques to delay disintegration and absorption in the gastrointestinal tract and thereby provide a sustained action over a longer period of time. For example, a time delay material such as glyceryl monostearate or glyceryl distearate alone or with a wax can be employed.

Formulations for oral use can also be presented as hard gelatin-containing or non-gelatinous capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil. Aqueous suspensions can contain the complex of the invention in admixture with excipients suitable for the manufacture of aqueous suspensions. Such excipients include suspending agents, dispersing or wetting agents, one or more preservatives, one or more coloring agents, one or more flavoring agents and one or more sweetening agents such as sucrose or saccharin.

Oil suspensions can be formulated by suspending the active ingredient in a vegetable oil, such as corn oil, sunflower oil, oil of evening primrose, olive oil, sesame oil or coconut oil, or in a mineral oil such as liquid paraffin. The oil suspension can contain a thickening agent, such as beeswax, hard paraffin or cetyl alcohol. Sweetening agents, such as those set forth above, and flavoring agents can be added to provide a palatable oral preparation. These compositions can be preserved by an added antioxidant such as ascorbic acid. Dispersible powders and granules of the invention suitable for preparation of an aqueous suspension by the addition of water provide the active ingredient in admixture with a dispersing or wetting agent, a suspending agent, and one or more preservatives. Additional excipients, for example sweetening, flavoring and coloring agents, can also be present.

Syrups and elixirs can be formulated with sweetening agents, such as glycerol, sorbitol, trehalose, or sucrose. Such formulations can also contain a demulcent, a preservative, a flavoring or a coloring agent.

The composition for parenteral administration can be in the form of a sterile injectable preparation, such as a sterile injectable aqueous or oleaginous suspension. This suspension can be formulated according to methods well known in the art using suitable dispersing or wetting agents and suspending agents. The sterile injectable preparation can also be a sterile injectable solution or suspension in a non-toxic parenterally-acceptable diluent or solvent, such as a solution in 1,3-butanediol. Suitable diluents include, for example, water, aqueous solution and isotonic sodium chloride solution. In addition, sterile fixed oils can be employed conventionally as a solvent or suspending medium. For this purpose, any bland fixed oil can be employed including synthetic mono or diglycerides. In addition, fatty acids such as oleic acid can likewise be used in the preparation of injectable preparations.

It will be appreciated that the amount of the compound may be combined with a carrier material to produce a single dosage form. Such forms will vary depending upon the host treated and the particular mode of administration.

In some aspects, strontium L-lactate may be added to food that is designed for animals. For example, the compound or composition may be added to and/or comprise a pet treat or biscuit, for example, a dog biscuit or a cat treat.

Aqueous suspensions may contain the compound disclosed herein in admixture with excipients suitable for the manufacture of aqueous suspensions. Such excipients include suspending agents, dispersing or wetting agents, one or more preservatives, one or more coloring agents, one or more flavoring agents and one or more sweetening agents such as sucrose or saccharin.

Controlled release vehicles are well known to those of skill in the pharmaceutical sciences. The technology and products in this art are variably referred to as controlled release, sustained release, prolonged action, depot, repository, delayed action, retarded release and timed release; the words "controlled release" as used herein is intended to incorporate each of the foregoing technologies.

Numerous controlled release vehicles are known, including biodegradable or bioerodable polymers such as polylactic acid, polyglycolic acid, and regenerated collagen. Known controlled release drug delivery devices include creams, lotions, tablets, capsules, gels, microspheres, liposomes, ocular inserts, minipumps, and other infusion devices such as pumps and syringes. Implantable or injectable polymer matrices, and topical formulations, from which active ingredients are slowly released, are also well known and can be used in the disclosed methods.

Controlled release preparations can be achieved by the use of polymers to form complexes with or absorb the strontium L-lactate. The controlled delivery can be exercised by selecting appropriate macromolecules such as polyesters, polyamino acids, polyvinylpyrrolidone, ethylenevinyl acetate, methylcellulose, carboxymethylcellulose, and protamine sulfate, and the concentration of these macromolecule as well as the methods of incorporation are selected in order to control release of active complex.

Controlled release of active complexes can be taken to mean any of the extended release dosage forms. The following terms may be considered to be substantially equivalent to controlled release, for the purposes of the present disclosure: continuous release, controlled release, delayed release, depot, gradual release, long term release, programmed release, prolonged release, programmed release, proportionate release, protracted release, repository, retarded release, slow release, spaced release, sustained release, time coat, time release, delayed action, extended action, layered time action, long acting, prolonged action, sustained action medications and extended release, release in terms of pH level in the gut and intestine, breakdown of the molecule and based on the absorption and bioavailability.

Hydrogels, wherein strontium L-lactate is dissolved in an aqueous constituent to gradually release over time, can be prepared by copolymerization of hydrophilic mono-olefinic monomers such as ethylene glycol methacrylate. Matrix devices, wherein strontium L-lactate is dispersed in a matrix of carrier material, can be used. The carrier can be porous, non-porous, solid, semi-solid, permeable or impermeable. Alternatively, a device comprising a central reservoir of strontium L-lactate surrounded by a rate controlling membrane can be used to control the release of the complex. Rate controlling membranes include ethylene-vinyl acetate copolymer or butylene terephthalate/polytetramethylene ether terephthalate. Use of silicon rubber or ethylene-vinyl alcohol depots is also contemplated.

Controlled release oral formulations are also well known. In one embodiment, the active complex is incorporated into a soluble or erodible matrix, such as a pill or a lozenge. In another example, the oral formulations can be a liquid used for sublingual administration. These liquid compositions can also be in the form a gel or a paste. Hydrophilic gums, such as hydroxymethylcellulose, are commonly used. A lubricating agent such as magnesium stearate, stearic acid, or calcium stearate can be used to aid in the tableting process.

Strontium L-lactate may also be delivery topically, including in a salve, cream, lotion, ointment, shampoo, or emulsion.

The amount of a strontium L-lactate composition that will be effective in the treatment of a particular disorder or condition disclosed herein will depend on the nature of the disorder or condition, and can be determined by standard clinical techniques. [See, by way of example, Wheater G, Elshahaly M, Tuck S P, Datta H K, van Laar J M. The clinical utility of bone marker measurements in osteoporosis. Journal of Translational Medicine. 2013; 11: 201.] In addition, in vitro or in vivo assays may optionally be employed to help identify optimal dosage ranges. Generally speaking, optimal dosage ranges will provide average serum or synovial concentrations of strontium ion sufficient to provide therapeutic benefit. In the absence of specific dosing information regarding bioavailability and dose, a dose of 2 mg per kilogram body weight may be used initially and increased incrementally until a dose sufficiently high to provide therapeutic benefits is achieved.

The compositions may be administered once, twice, or three times per day. In some aspects, the compositions are administered four times a day. For example, the compositions may be administered before, after, or during a meal. Dosing for oral administration may be with a regimen calling for single daily dose, or for a single dose every other day, or for a single dose within 72 hours of the first administered dose, or for multiple, spaced doses throughout the day. The active agents which make up the therapy may be administered simultaneously, either in a combined dosage form or in separate dosage forms intended for substantially simultaneous oral administration. The active agents which make up the therapy may also be administered sequentially, with either active component being administered by a regimen calling for two-step ingestion. Thus, a regimen may call for sequential administration of the active agents with spaced-apart ingestion of the separate, active agents. The time period between the multiple ingestion steps may range from a few minutes to as long as about 72 hours, depending upon the properties of each active agent such as potency, solubility, bioavailability, plasma half-life and kinetic profile of the agent, as well as depending upon the age and condition of the patient. The active agents of the therapy whether administered simultaneously, substantially simultaneously, or sequentially, may involve a regimen calling for administration of one active agent by oral route and the other active agent by intravenous route. Whether the active agents of the therapy are administered by oral or intravenous route, separately or together, each such active agent will be contained in a suitable pharmaceutical formulation of pharmaceutically-acceptable excipients, diluents or other formulations components.

The active ingredients (i.e., strontium L-lactate and other pharmaceutical or supplemental ingredients that may be present) can be administered by the oral route in solid dosage forms, such as tablets, capsules, lozenges, pastes, and powders, or in liquid dosage forms, such as elixirs, syrups, and suspensions. Each active ingredient can be administered by the parenteral route in liquid dosage forms. The pharmaceutical composition is preferably made in the form of a dosage unit containing a particular amount of each active ingredient. One most preferred oral dosage form of a composition of the present application is an admixture of powders contained within a sachet. Because a composition of the present application is not hygroscopic and has no repugnant taste or odor, the admixture of powders comprising a composition of the present application can be sprinkled on food or stirred into beverages to enhance ease of use and support high levels of compliance with daily dosage regimens.

In general, the pharmaceutical dosage forms of compositions of this application can be prepared by conventional techniques, as are described in Remington's Pharmaceutical Sciences, a standard reference in this field [Gennaro A R, Ed. Remington: The Science and Practice of Pharmacy. 20th Edition. Baltimore: Lippincott, Williams & Williams, 2000]. For therapeutic purposes, the active components of this combination therapy application are ordinarily combined with one or more adjuvants appropriate to the indicated route of administration. The components may be admixed with lactose, sucrose, starch powder, cellulose esters of alkanoic acids, cellulose alkyl esters, talc, stearic acid, magnesium stearate, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropyl methylcellulose. Solid dosage forms can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Both the solid and liquid oral dosage forms can contain coloring and flavoring to increase patient acceptance. Other adjuvants and modes of administration are well and widely known in the pharmaceutical art.

Rationale for Use of the Pharmaceutical Quality Strontium L-Lactate Compositions of the Present Invention The inventor believes that it is chemically reasonable to use a composition of the invention as the strontium-containing nutritional supplement or medicament in each of the known applications where strontium ion has exhibited benefit and safety. By way of example, when a strontium salt such as strontium ranelate is used as a treatment for bone disorders, the strontium ion, the active ingredient in a strontium salt, is thought to have a unique mechanism of action mediated by a cation-sensing receptor (e.g., the calcium-sensing receptor) and the RANK/RANKL/OPG pathway. Strontium ion appears to beneficially increase pre-osteoblast proliferation, osteoblast differentiation, collagen type I synthesis, and bone matrix mineralization while inhibiting osteoclast differentiation and activation. This proposed dual mechanism of action yields significant positive effects on bone quality as assessed by clinical diagnostic techniques such as analytical determinations of biological markers, tissue biopsies, high-resolution peripheral quantitative computed tomography (hr-pQCT) and microCT, as well as x-ray fluorescence (XRF). Both animal and human studies have shown that strontium is almost exclusively found in newly formed bone where it has been incorporated as apatite crystals. Moreover, oral administration of strontium has improved bone architecture and strength, repairing defects that had compromised these characteristics of normal bone. [See: (a) Saidak Z, Marie P J. Strontium signaling: molecular mechanisms and therapeutic implications in osteoporosis. Pharmacol Ther. 2012 November; 136(2): 216-26. PubMed PMID: 22820094. (b) Saidak Z, Marie P J. Strontium signaling: molecular mechanisms and therapeutic implications in osteoporosis. Pharmacol Ther. 2012 November; 136(2): 216-26. PubMed PMID: 22820094. (c) Karsdal M A, Bay-Jensen A C, Lories R J, Abramson S, Spector T, Pastoureau P, Christiansen C, Attur M, Henriksen K, Goldring S R, Kraus V. The coupling of bone and cartilage turnover in osteoarthritis: opportunities for bone antiresorptives and anabolics as potential treatments? Ann Rheum Dis. 2014 February; 73(2): 336-48. PubMed PMID: 24285494. (d) Radojčić M R, Thudium C S, Henriksen K, Tan K, Karlsten R, Dudley A, Chessell I, Karsdal M A, Bay-Jensen A C, Crema M D, Guermazi A. Biomarker of extracellular matrix remodelling C1M and proinflammatory cytokine interleukin 6 are related to synovitis and pain in end-stage knee osteoarthritis patients. Pain. 2017 Mar. 22. Pain. 2017 Mar. 22. doi: 10.1097/j.pain.0000000000000908. PubMed PMID: 28333699. (e) Valdes A M, Meulenbelt I, Chassaing E, et al. Large scale meta-analysis of urinary C-terminal telopeptide, serum cartilage oligomeric protein and matrix metalloprotease degraded type II collagen and their role in prevalence, incidence and progression of osteoarthritis. Osteoarthritis Cartilage. 2014; 22(5): 683-689. (f) van Spil W E, DeGroot J, Lems W F, Oostveen J C M, Lafeber F P J G. Serum and urinary biochemical markers for knee and hip-osteoarthritis: a systematic review applying the consensus BIPED criteria. Osteoarthritis Cartilage. 2010; 18(5): 605-612. (g) Patraa D, Sandell L J. Recent advances in biomarkers in osteoarthritis. Curr Opin Rheumatol. 2011; 23(5): 465-470. (h) Dam E B, Byrjalsen I, Karsdal M A, Qvist P, Christiansen C. Increased urinary excretion of C-telopeptides of type II collagen (CTX-II) predicts cartilage loss over 21 months by MRI. Osteoarthritis Cartilage. 2009; 17(3): 384-389. (i) Querido W, Rossi A L, Farina M. The effects of strontium on bone mineral: A review on current knowledge and microanalytical approaches. Micron. 2016 January; 80: 122-34. PubMed PMID: 26546967.]

ADVANTAGES OF THE INVENTION

Briefly summarized, the present invention provides stable, water-soluble, pharmaceutical quality strontium L-lactate compositions that substantially contain the L-enantiomer of lactate. Further, the compositions contain at most trace levels of metal contaminants such as aluminum, arsenic, barium, cadmium, chromium, lead, mercury, and thallium. Compositions of the invention have no repugnant odor. Solutions of compositions of the invention in water and aqueous buffers are readily prepared because the compositions have water-solubility of about 33 g/100 mL. The solutions are not bitter and cause no off-flavor. All of these characteristics support compliance with daily dosage regimens, particularly regimens which extend over many years.

The inventor directed completion of a clinical study using pharmaceutical quality strontium L-lactate. She discovered that a strontium L-lactate composition is more rapidly and efficiently absorbed by men and women as test subjects as compared to the bioavailability of a water-insoluble strontium salt such as strontium ranelate that is disclosed in U.S. Pat. No. 7,595,342. The average concentration of strontium in the serum reached a maximum about 3 hr after ingesting a solution of the strontium L-lactate in water. The average serum concentration of strontium achieved by ingesting a 170 mg dose of strontium as the L-lactate approximately equaled the serum concentration of strontium achieved by ingesting a 680 mg dose of strontium as the ranelate. Thus, the greater bioavailability of the water-soluble strontium L-lactate over conventional water-insoluble strontium salts was confirmed. During the clinical study the subjects reported no distaste as a result of ingesting the aqueous solution of the composition and experienced no adverse effects after ingesting any of three escalating doses of the strontium L-lactate composition.

As a consequence of the water-solubility of compositions of the invention and of their greater bioavailability, significantly lower doses of the strontium L-lactate composition provide therapeutically effective doses of strontium ion. In other words, 170 mg doses of the water-soluble strontium L-lactate composition provided serum strontium concentrations approximately equal to the serum concentrations of strontium provided by 680 mg of water-insoluble strontium ranelate that are known to have therapeutic benefits. Thus, the inventor believes that subjects ingesting formulations containing compositions of the instant invention will experience beneficial improvements in bone health. In addition, reduction in bone pain and increased joint flexibility are expected.

Moreover, subjects using her strontium L-lactate compositions are expected to experience fewer adverse effects than are observed following administration of water-insoluble strontium salts such as strontium ranelate. Whereas strontium ranelate tastes bitter, strontium L-lactate, either in solid form or in solution, has no repugnant or bitter taste. Thus, there is no need to formulate with taste masking agents such as aspartame. The L-lactate anion of strontium L-lactate compositions is a physiological anion that does not cause rashes. In contrast, synthetic anions such as ranelate contain structural features that lend themselves to adverse physiological responses such as skin rashes. Further, high concentrations of strontium ion increase the risk of platelet activation. Therefore, the ability to administer lower doses of strontium L-lactate compositions to obtain equivalent therapeutic benefit is expected to improve the benefit to risk ratio.

Significantly, the strontium ion inhibits the formation and/or activity of inflammatory cytokines and matrix metalloproteinases. [See: (a) de Melo Nunes R, Martins M R, da Silva Junior F S, de Melo Leite A C, Girão V C, de Queiroz Cunha F, Marinho A L, Pinto A C, Rocha F A. Strontium ranelate analgesia in arthritis models is associated to decreased cytokine release and opioid-dependent mechanisms. Inflamm Res. 2015 October; 64(10):781-7. PubMed PMID: 26245235. (b) Esat Korgali, Gokce Dundar, Kubra Acikalin Coskun, et al., "Effect of Strontium Chloride on Experimental Bladder Inflammation in Rat," International Scholarly Research Notices, vol. 2014, Article ID 369292, 2014. doi:10.1155/2014/369292.] Therefore, administration of strontium L-lactate compositions is expected to provide therapeutic benefits for the treatment of cartilage disorders such as osteoarthritis or torn ligaments. Moreover, administration of these compositions is expected to beneficially reduce the activity of inflammatory enzymes and cytokines in the gastrointestinal tract.

The inventor expects that her compositions will be especially beneficial for three groups of patients. For example, subjects having bone or joint disorders (such as osteoporosis or osteoarthritis, for example) who consume medicaments to reduce stomach acidity will be less able to dissolve water-insoluble treatments like strontium ranelate that require exposure to acidic gastric fluid for strontium release. As a result, these water-insoluble salts will be less effective in providing the quantity of strontium ion needed for therapeutic efficacy. The inventor believes that the water-solubility of her strontium L-lactate composition is independent of gastric acidity and will provide a therapeutic concentration of strontium ion to the bone and joint irrespective of the user's gastric pH.

Likewise, today there are no effective treatments for osteonecrosis of the jaw caused by lengthy use of bone resorption inhibitors (anti-resorptives). The inventor has discovered that a low daily oral dose of a strontium L-lactate composition of the invention reduced the injury and pain associated with osteonecrosis of the jaw caused by treatment with alendronate as disclosed in Example 11. The test subject experienced deterioration of the jawbone sufficient to loosen her teeth and cause pain when chewing. She received a 200 mg dose of strontium as the L-lactate each day, taken separately from food. A 500 mg dose of supplemental calcium was taken each day separately from the dose of the strontium L-lactate. Over a 3-month period, the subject receiving this treatment experienced a restoration of the jawbone sufficient to set the teeth more firmly and reduce the pain associated with chewing. At the same time, she experienced increased flexibility of osteoarthritic hands and fingers, an improvement also associated with the strontium L-lactate treatment. The benefits were so remarkable that the subject continued treatment for at least 8 months, with continuing resolution of the bone and cartilage defects. She reported no side effects.

Further, the inventor has discovered that ingestion of a low daily oral dose of a strontium L-lactate composition of the invention corrects imbalances in bone turnover that are characteristic of both high-turnover and low-turnover osteodystrophy. High-turnover osteodystrophy is exhibited, by way of example, in women who are post-menopausal and for 6 months to 1 year post-menopause. This disorder is characterized by high bone resorption by osteoclasts and low bone remodeling by osteoblasts. The condition is monitored by rises in serum or urine concentrations of markers of bone resorption such as Type I collagen telopeptides (e.g., NTX-1, CTX-1, and CTX-MMP), hydroxyproline, hydroxylysine, galactosyl hydroxylysine, glucosyl galactosyl hydroxylysine, pyridinoline, and deoxypyridinoline to above normal values. Concurrently decreases in the serum concentrations of bone-specific alkaline phosphatase are observed. Serum concentrations of parathyroid hormone of nine times normal values may be observed. High-turnover osteodystrophy causes changes in material composition and nanomechanical properties different from normal bone quality. The disorder is usually treated by administration of anti-resorptive agents such as bisphosphonates.

Low-turnover osteodystrophy is exhibited, by way of example, in women who are more than 1 year post-menopausal and in women who have been treated with bisphosphonate therapy for more than 6 months. Both bone resorption and bone remodeling are suppressed. Low-turnover osteodystrophy causes adverse changes in microstructural parameters in bone. Patients having low-turnover osteodystrophy frequently experience bone pain. The disorder is usually treated by administration of anabolic agents such as hormone replacement therapy or teraparatide. The duration of treatment is limited by side effects of these anabolic agents.

The inventor has discovered that ingestion of a low daily dose of a strontium L-lactate composition of the invention normalizes the changes in bone quality resulting from both high- and low-turnover osteodystrophy. This discovery is particularly significant for patients who have been treated with anti-resorptive agents such as bisphosphonates, since it is known that these agents cause osteonecrosis of the jawbone and other structural bones that result in unexpected risk and incidence for fracture, effects which may persist after treatment with the anti-resorptive agent has stopped. This is particularly significant for patients who exhibit low-turnover osteodystrophy as well, since it is known that the current anabolic agents may be administered for limited periods of time (e.g., 2 years or less) whereas strontium ion may be administered beneficially for periods as long as 10 years without causing adverse effects.

When a daily dose of strontium L-lactate of about 200 mg strontium is administered to adult humans with calcium, chondroitin preparations, glucosamine, vitamin D, and vitamin K, the inventor believes that the synergies among these therapeutic agents will be optimized if the daily doses of calcium are in the range 250 to 500 mg, of vitamin D are in the range 400 to 1000 IU, and of vitamin K are in the range 300 micrograms to 50 milligrams.

EXAMPLES

The invention is illustrated by way of Examples which follow.

Example 1: Conventional Method for the Preparation of Strontium Lactate

Taken together, Examples 1 and 3 of U.S. Pat. No. 7,589,235 disclose a method for the synthesis of strontium salts, including strontium lactate. The method, which is disclosed in Examples 1 and 3 of U.S. Pat. No. 7,589,235, consists of the following steps.

Step 1: In a glass beaker of 100 mL volume, 5 g of the sodium salt of lactic acid was dissolved in a small volume of water that was slightly heated at temperatures not greater than 30-50° C. The final volume was 20-50 mL of a clear solution.

Step 2: In another beaker 10 g of $SrCl_2$ hexahydrate (Sigma-Aldrich) was dissolved in 20 mL of water to provide a clear solution.

Step 3: This latter solution was slowly added into the first solution of the dissolved sodium salt until 1.1 equivalents of $SrCl_2$ had been added. A clear and colorless solution having a volume of 50-100 mL resulted.

Step 4: After standing at room temperature for hours or days, Example 1 discloses that this procedure failed to provide strontium lactate. The lactate salt was isolated by addition of an excess of strontium chloride, after which large crystals of strontium lactate were obtained by slow evaporation of the solvent.

Step 5: In Example 3, '235 discloses that in order to accelerate the crystallization, an alcohol such as methanol or ethanol was added to achieve a volume percent of from 5-10% volume/volume (v/v) to 50-60% v/v. In the absence of added alcohol, the classic conventional process provided at most less than 40% yield of strontium salt. In the presence of added alcohol, the process disclosed in '235 provided yields that exceeded 80%.

In '235 quality and purity are defined as an absence of strontium carbonate in the product. Tests for quality and purity such as strontium analysis, HPLC analysis of lactate, HPLC analysis of organic impurities, determination of sterility and absence of endotoxins, are lacking.

The inventor repeated the steps of the conventional preparation disclosed in '235 using 5 g of the sodium salt of L-lactic acid (Sigma Aldrich) and 0.45 equivalent of strontium chloride (Sigma Aldrich). Upon repetition of Step 4, no precipitate was formed when an excess of strontium chloride was not used. (Excess strontium chloride is a potential contaminant of the desired pharmaceutical quality product.) Instead, the inventor followed the guidance of Step 5 of the conventional preparation. Addition of multiple volumes of methanol, an improvement disclosed in Example 3 of U.S. Pat. No. 7,589,235 as one capable of increasing yields to greater than 80%, provided a larger volume of clear and colorless solution. No solid precipitated. This lack of utility of alcohol-induced precipitation confirms the report in the "Dispensatory of the United States" (1907), which states that strontium lactate is highly soluble in water and alcohols such as methanol and ethanol. Apparently, the utility of alcohol-induced precipitation disclosed in US '235 applies only to strontium salts of higher molecular weight carboxylates and does not apply to strontium salts of low molecular weight carboxylates such as lactate.

Example 2: Preparation of Strontium L-Lactate of the Present Invention by Neutralization of L-Lactic Acid A clear and colorless solution of 9 grams (0.1 mole) of L-lactic acid (Alfa Aesar) was prepared in an initial volume of 10 mL of deionized water. (Both the L-lactic acid and the water were analyzed and shown to contain at most trace levels of metal contaminants such as aluminum, arsenic, barium, calcium, cadmium, chromium, lead, mercury, and thallium.) Then 7.6 g (0.05 mole) of strontium carbonate (Strem) was added in small portions to the stirred lactic acid solution. (The strontium carbonate was analyzed and shown to contain at most trace levels of metal contaminants such as aluminum, arsenic, barium, calcium, cadmium, chromium, lead, mercury, and thallium.) After each addition, sufficient time was allowed for carbon dioxide gas to be released from solution. Periodically water was used to wash any remaining particulate back into solution. The resulting solution was stirred overnight to ensure complete reaction. Some solid strontium carbonate remained. The particulate was so fine that it could not be removed by filtration and was compacted into a pellet by centrifugation of the solution. The clear supernatant, an aqueous solution of strontium L-lactate, was separated from the pellet. Six volumes of acetone were added to the supernatant solution, and a white solid formed. The slurry was refrigerated to maximize precipitation of the solid. The solid was isolated by filtration, washed with fresh acetone, and dried. The product, strontium L-lactate trihydrate, was obtained in 92% yield. Tests for quality and purity such as strontium analysis, NMR and HPLC analysis of L-lactate, HPLC analysis of organic impurities, determination of sterility and absence of endotoxins, were performed.

Example 3: Preparation of Strontium L-Lactate of the Present Invention by Neutralization of L-Lactic Acid A clear and colorless solution of 9.2 grams (0.1 mole) of L-lactic acid (Alfa Aesar) was prepared in a volume of 15 mL of deionized water. (Both the L-lactic acid and the water were analyzed and shown to contain at most trace levels of metal contaminants such as aluminum, arsenic, barium, calcium, cadmium, chromium, lead, mercury, and thallium.) Then 5.18 g (0.05 mole) of strontium oxide (Strem) was added in small portions to the stirred lactic acid solution. (The strontium oxide was analyzed and shown to contain at most trace levels of metal contaminants such as aluminum, arsenic, barium, calcium, cadmium, chromium, lead, mercury, and thallium.) During the addition, heat was released and the stirred solution became hot. Strontium oxide was added in portions so that a reaction temperature of less than about 60° C. was maintained. After the addition was complete, the solution was clear and colorless but as it cooled, a white precipitate formed. The slurry was stirred overnight to ensure complete reaction. Three volumes of acetone were added and the solid was isolated by filtration, washed with fresh acetone, and dried. The product, shiny, white, crystalline strontium L-lactate trihydrate, was obtained in 95% yield. Tests for quality and purity such as strontium analysis, NMR and HPLC analysis of L-lactate, HPLC analysis of organic impurities, determination of sterility and absence of endotoxins, were performed.

Example 4: Preparation of Strontium L-Lactate of the Present Invention by Neutralization of L-Lactic Acid A clear and colorless solution of 9 grams (0.1 mole) of L-lactic acid (Alfa Aesar) was prepared in an initial volume of 10 mL of deionized water. (Both the L-lactic acid and the water were analyzed and shown to contain at most trace levels of metal contaminants such as aluminum, arsenic, barium, calcium, cadmium, chromium, lead, mercury, and thallium.) Then 5.6 g (0.046 mole) of strontium hydroxide (American Elements) was added in small portions to the stirred lactic acid solution. (The strontium hydroxide was analyzed and shown to contain at most trace levels of metal contaminants such as aluminum, arsenic, barium, calcium, cadmium, chromium, lead, mercury, and thallium.) The resulting solution was stirred for an hour to ensure complete reaction. The solution was filtered, and three volumes of acetone were added. A white solid formed. The slurry was refrigerated to maximize precipitation of the solid. The solid was isolated by filtration, washed with fresh acetone, air-dried. The product, strontium L-lactate trihydrate, was obtained in 90% yield. Tests for quality and purity such as strontium analysis, NMR and HPLC analysis of L-lactate, HPLC analysis of organic impurities, determination of sterility and absence of endotoxins, were performed.

Example 5. Preparation of Strontium L-Lactate of the Present Invention by Cation Exchange with Sodium L-Lactate A clear and colorless solution of 9.8 grams (0.08 mole) of sodium L-lactate (Sigma Aldrich) was prepared in 25 mL of deionized water. (Both the sodium L-lactate and the water were analyzed and shown to contain at most trace levels of metal contaminants such as aluminum, arsenic, barium, calcium, cadmium, chromium, lead, mercury, and thallium.) A solution of 11.66 g (0.04 mole) of strontium chloride hexahydrate (Sigma Aldrich) was prepared in 15 mL of deionized water. (The solution cools as the strontium salt dissolves.) (The strontium chloride hexahydrate was analyzed and shown to contain at most trace levels of metal contaminants such as aluminum, arsenic, barium, calcium, cadmium, chromium, lead, mercury, and thallium.) The strontium-containing solution was added to the stirred sodium L-lactate solution and a clear and colorless solution was obtained. Six volumes of acetone were added to the solution, and a white solid formed. The solid was isolated by filtration, washed with an 80:20 (v/v) solution of acetone:water to remove sodium chloride, and dried. The product, strontium L-lactate trihydrate, was obtained in 70% yield. Tests for quality and purity such as strontium analysis, NMR and HPLC analysis of L-lactate, HPLC analysis of organic impurities, determination of sterility and absence of endotoxins, were performed.

Example 6. Determination of Optical Rotation

The optical rotation of an aqueous solution of 1 g of strontium L-lactate per 100 mL was determined with a path length of 100 mm and a temperature of 25° C. A wavelength of incident light of 589 nm was used. The optical rotation of the sample was determined to be −9.0°.

Example 7. Stability of the Compositions

When a strontium L-lactate trihydrate composition was heated at 110° C. under vacuum, water of hydration was removed and a strontium L-lactate anhydrous composition was obtained. Strontium L-lactate trihydrate compositions were stable during storage at 25° C./60% relative humidity. Both trihydrate and anhydrous compositions were stable on exposure to light.

Example 8. Strontium L-Lactate—Bioavailability Study

In an unblinded clinical study, 10 subjects (5 men and 5 women) were screened in order to qualify for enrollment in a sequential dose escalation study to assess human pharmacokinetics of orally administered strontium L-lactate of the invention. The study was approved by an Institutional Review Board. The subjects who were enrolled were healthy men and women 18-65 years of age, inclusive, with a body mass index (BMD) 18 to 31.9 kg/m$^2$ and a body weight of >60 kg. Each provided informed consent to participate in the study.

On the day of dose administration, the subjects arrived at the clinic fasted. Their qualifications for enrollment were reviewed to ensure compliance. Immediately prior to administration of the test article, an indwelling venous catheter was placed and a blood sample was withdrawn into a trace metal-free tube (the t=0 sample). Following ingestion of the test article (170 mg of strontium as strontium L-lactate of the invention dissolved in 100 mL distilled water), additional blood samples were withdrawn at t=1, 2, 3, 4, 5, 8, and 12 hours. After drinking the test article solution, fasting continued for 2 hours. During the day, however, subjects were provided usual and customary meals. Potential adverse events were monitored.

Each blood sample was stored appropriately until all samples had been collected for the day. Then the blood samples were centrifuged to separate the serum, and each serum sample was transferred into two trace metal-free vials. The vials were shipped to an independent analytical laboratory for serum strontium analyses.

One week later, on the day of dose administration, the same subjects arrived at the clinic fasted. Their qualifications for enrollment were reviewed to ensure compliance. Immediately prior to administration of the test article, an indwelling venous catheter was placed and a blood sample was withdrawn into a trace metal-free tube (the t=0 sample). Following ingestion of the test article (340 mg of strontium as strontium L-lactate of the invention dissolved in 100 mL distilled water), additional blood samples were withdrawn at t=1, 2, 3, 4, 5, 8, and 12 hours. After drinking the test article solution, fasting continued for 2 hours. During the day, however, subjects were provided usual and customary meals. Potential adverse events were monitored.

Each blood sample was stored appropriately until all samples had been collected for the day. Then the blood samples were centrifuged to separate the serum, and each serum sample was transferred into two trace metal-free vials. The vials were shipped to an independent analytical laboratory for serum strontium analyses.

One week later, on the day of dose administration, the same subjects arrived at the clinic fasted. Their qualifications for enrollment were reviewed to ensure compliance. Immediately prior to administration of the test article, an indwelling venous catheter was placed and a blood sample was withdrawn into a trace metal-free tube (the t=0 sample). Following ingestion of the test article (680 mg of strontium as strontium L-lactate of the invention dissolved in 100 mL distilled water), additional blood samples were withdrawn at t=1, 2, 3, 4, 5, 8, and 12 hours. After drinking the test article solution, fasting continued for 2 hours. During the day, however, subjects were provided usual and customary meals. Potential adverse events were monitored.

Each blood sample was stored appropriately until all samples had been collected for the day. Then the blood samples were centrifuged to separate the serum, and each serum sample was transferred into two trace metal-free vials. The vials were shipped to an independent analytical laboratory for serum strontium analyses.

Figure 2:
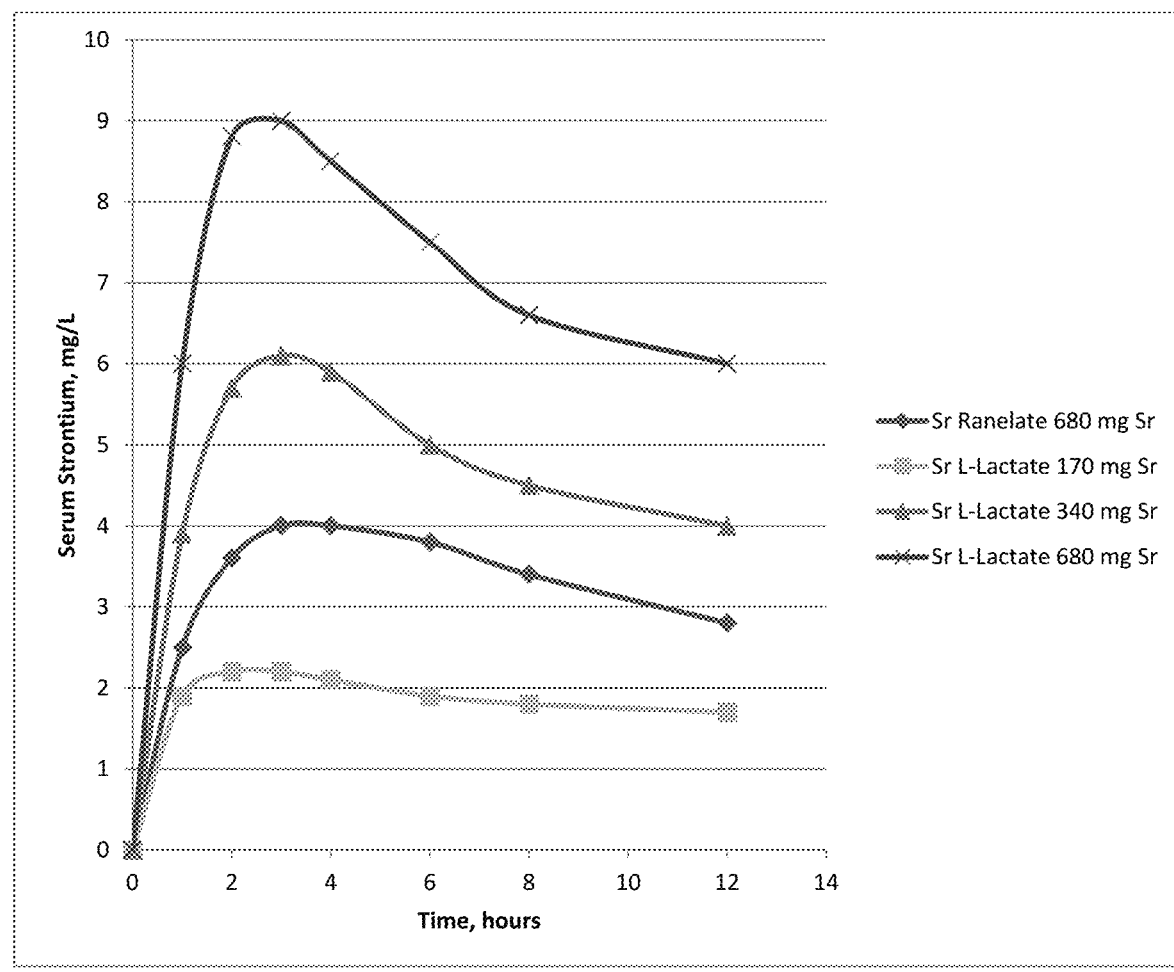
FIG. 2 is a graphical display of the pharmacokinetics of strontium absorption into the systemic circulation after oral administration of a strontium L-lactate composition of the invention to men and women as disclosed in Example 8. The display includes a comparison to the pharmacokinetics of strontium absorption after oral administration of strontium ranelate to men and women as disclosed in U.S. Pat. No. 7,595,342.
Figure 3:
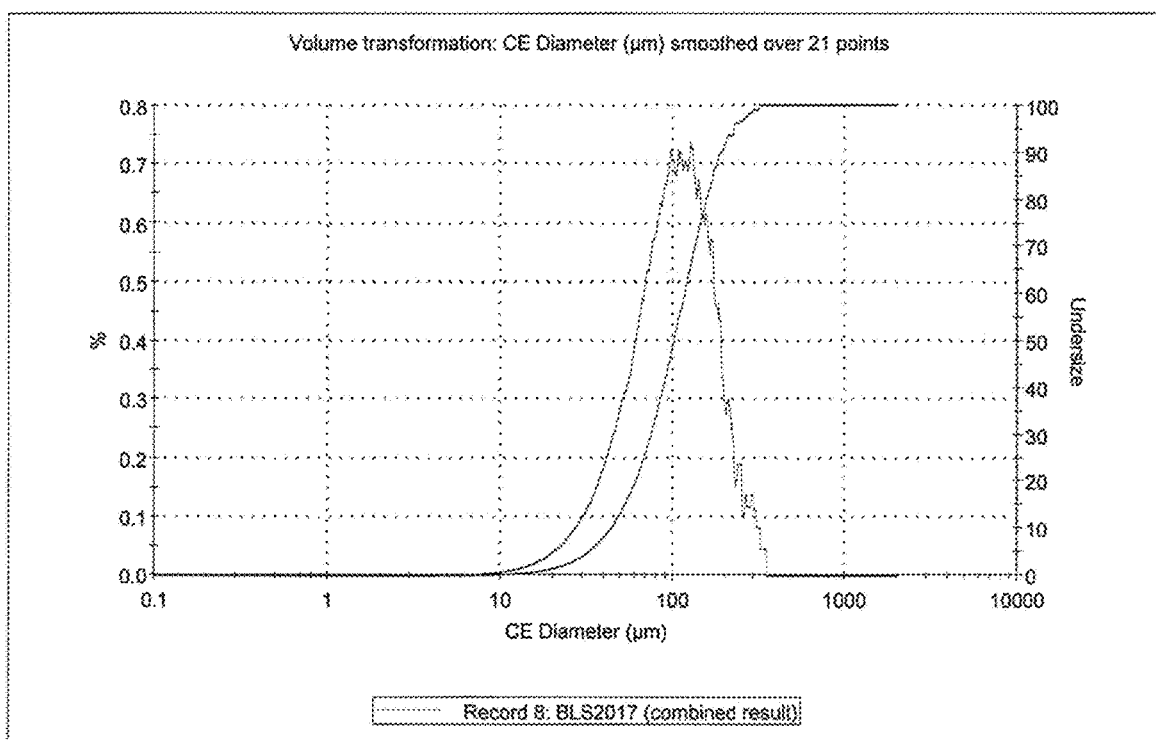
FIG. 3 is a graphical display of particle size distribution of strontium L-lactate of the invention.

Results are summarized in Tables 1-2 and are graphically presented in FIG. 2.

TABLE 1

Subject Disposition

| Number of Subjects | Overall |
|---|---|
| Randomized | 10 (100%) |
| Completed Study | 10 (100%) |
| Did Not Complete Study | 0 (0%) |
| Included in: | |
| mITT Population | 10 (100%) |
| Per Protocol Population | 10 (100%) |
| Discontinued due to: | |
| Adverse Event | 0 (0%) |
| Death | 0 (0%) |
| Withdrawal of Consent | 0 (0%) |
| Lost to Follow-up | 0 (0%) |
| Other | 0 (0%) |

TABLE 2

Pharmacokinetics

| Dose of Strontium (mg) | 170 | 340 | 680 |
|---|---|---|---|
| Number of Subjects | 10 | 10 | 10 |
| Maximum serum concentration ($C_{max}$; mg Sr/L) | | | |
| Mean | 2.6 | 6.3 | 9.3 |
| Std Dev | 0.6 | 1.7 | 2.1 |
| Time to $C_{max}$, (h) | | | |
| Mean | 3.0 | 3.2 | 2.8 |
| Std Dev | 1.1 | 0.4 | 0.7 |
| Rate of elimination (K; $h^{-1}$) | | | |
| Mean | 0.06 | 0.06 | 0.05 |
| Std Dev | 0.01 | 0.01 | 0.01 |
| Half-life ($T_{1/2}$) | | | |
| Mean | 12.3 | 12.1 | 14.0 |
| Std Dev | 2.3 | 2.6 | 3.2 |
| Area under the curve ($AUC_{0-\infty}$; mg Sr/L · h) | | | |
| Mean | 47.8 | 115.6 | 185.0 |
| Std Dev | 13.1 | 34.0 | 42.1 |
| Oral Bioavailability | | | |
| Mean | 0.94 | 0.93 | 0.94 |
| Std Dev | 0.04 | 0.03 | 0.02 |

Example 9. Strontium L-Lactate—Clinical Pharmacology

After oral administration to fasted men and women, the absorption of Sr was dose-dependent and exhibited a less than proportional increase in $C_{max}$ and AUC was observed over a dose range of 0.17 to 0.68 g of a strontium L-lactate composition of the invention. For all doses $T_{max}$ occurs between 2.8 and 3.2 hours. $C_{max}$ after a 170 mg single dose is approximately 2.6 mg Sr/L. The fraction absorbed dose of strontium ranged from about 28% to about 33%.

Example 10. Strontium L-Lactate—Efficacy Study

A 89 year old female subject suffered from latent osteonecrosis of the jaw as a result of several years of alendronate treatment for osteoporosis. In addition to loose teeth and jaw pain during chewing due to the osteonecrosis, she suffered from osteoarthritis. Her dentist advised her that the necrosis was so serious she would lose several teeth and might have to change from a normal diet to a soft-food diet. Her arthritis was so severe that she had to give up crocheting and knitting, hobbies she had enjoyed for many years. This prognosis had significantly reduced her quality of life. She requested access to strontium L-lactate of the present invention. Each day she ingested about 200 mg of strontium as strontium L-lactate of the invention, typically before meals and separate from other medications. After 3 months of treatment, she reported that her teeth were more set in her jawbone and that she experienced less pain when chewing. In addition, she reported that the stiffness and pain of her osteoarthritis had significantly abated, and she was able to resume crocheting and knitting. Her treatment continued for 8 months with similar improvements.

Example 11: Strontium L-Lactate—Clinical Study

In a double-blind clinical study, 80 subjects are divided into two groups (n=40). The control group receives a daily supplement containing 1.8 g of sodium L-lactate (placebo). The trial group receives a daily supplement containing 200 mg of strontium as strontium L-lactate. Subjects are eligible for inclusion if they have a femoral neck BMD less than 0.600 g/cm$^2$ (T-score<−2.5 on the Slosman reference range, equivalent to a T-score<−2.2 on the widely adopted NHANES III (Third National Health and Nutrition Examination Survey) hip reference range) and are aged 74 y or over, or are between 70 y and 74 y and have at least one additional risk factor such as a history of previous osteoporotic fracture or a maternal history of fracture. The subjects are randomized to receive either strontium L-lactate (0.55 g/day) or placebo, and also receive calcium and vitamin K supplements. All non-vertebral fractures will be recorded with the exception of the coccyx, skull, jaw, face, phalanx (fingers and toes) and ankle, since these latter are not regarded as being related to osteoporosis. Over the 3 year follow-up period strontium L-lactate treatment is expected to achieve a significant reduction in all non-vertebral fractures. In addition, for the principal non-vertebral fracture sites (hip, wrist, pelvis, sacrum, ribs, sternum, clavicle, humerus) a significant reduction in fracture risk is expected. The incidence of adverse effects is expected to be comparable to or less than the incidence observed in those receiving placebo. In interviews during the study, it is expected that the subjects receiving strontium will remark that the pains in their bones had diminished and their ability to move around had improved significantly.

Example 12. Strontium L-Lactate—Bioavailability in Dogs

Twelve healthy dogs meeting the selection criteria (Table 3) are included in the study. Equal distributions of male and female dogs are included. Prospective candidate dogs are evaluated by physical examination, clinical chemistry (total protein, albumin, globulin, albumin/globulin ratio, blood urea nitrogen, creatinine, blood urea nitrogen/creatinine ratio, glucose, alanine aminotransferase, and alkaline phosphatase) and hematology (platelet count, hemoglobin, hematocrit, mean corpuscular volume, mean corpuscular hemoglobin, mean corpuscular hemoglobin count, red blood cell count, and white blood cell count with differential [lymphocytes, monocytes, neutrophils, eosinophils, and basophils]), CBC, PT, APTT, TEG (if available), blood gas analysis, blood lactate and basic biochemistry.

TABLE 3

SELECTION CRITERIA

| Category | Selection Criteria |
| --- | --- |
| Inclusion | Healthy, privately owned or mongrel dogs, 18 months of age or older, weighing 10-100 pounds and having a Body Condition Score (BCS) equivalent to 15-29% body fat. |
| Potential Inclusion | Dogs that are currently receiving prescription or over-the-counter analgesic medications or NSAIDs daily: only eligible to participate in the study following a 14-day washout period for NSAIDs, a 7-day washout period for narcotics, and a 90-day washout period for injected steroids.<br>Dogs currently receiving vitamins, multi-vitamins, or supplements or consuming a "joint health" diet (i.e., those containing glucosamine, chondroitin sulfate, curcumin, methylsulfonylmethane, etc.) will only be eligible to participate in the study following a 7-day washout period. |
| Exclusion | Dogs having a known confounding immune-mediated (e.g., lupus), known infectious (e.g., Lyme disease), known neurological, or known neoplastic disease or condition.<br>Dogs having a significant injury within the past 3 months, or pregnant or nursing female dogs.<br>Subjects participating in any other research study involving an investigational product (drug, device, or biologic) or a new application of an approved product, within 30 days of screening. |

Eligible subjects are fasted overnight and the next morning each receives a single oral dose of 340 mg strontium as strontium L-lactate. Blood samples are drawn into trace metal-free tubes prior to dosing and 1, 2, 3, 4 and 6 hr after dosing. Food and drink are provided ad libitum beginning 1 hr after dosing. Behavior is monitored for 12 hr after dosing. Blood samples are stored refrigerated until they are centrifuged to separate the serum. Serum samples are analyzed for strontium.

One week later, the same subjects are fasted overnight and the next morning receive a single oral dose of 680 mg strontium as strontium L-lactate. Blood samples are drawn into trace metal-free tubes prior to dosing and 1, 2, 3, 4 and 6 hr after dosing. Food and drink are provided ad libitum beginning 1 hr after dosing. Behavior will be monitored for 12 hr after dosing. Blood samples are stored refrigerated until they are centrifuged to separate the serum. Serum samples are analyzed for strontium.

Statistical Analysis. Descriptive statistics (i.e., number of subjects, minimum and maximum, median, interquartile limits, mean, and SEM) are presented for all the continuous outcomes for each dose level. A time response graph depicting mean and SEM of serum strontium concentrations for each dose is also presented.

Incremental area under the curve (AUC) is calculated for serum strontium using the linear trapezoidal rule of the standard non-compartmental analysis. Rate of elimination, half-life and iAUC are also calculated.

Expected Outcomes. Strontium L-lactate exhibits a bioavailability and general safety in the dog similar to the corresponding properties found in humans.

Example 13. Effect of Strontium L-Lactate on Osteoarthritis in Dogs

Twelve dogs meeting the selection criteria are included in the study. An equal distribution of male and female dogs are included. All dogs are evaluated by physical examination, clinical chemistry (total protein, albumin, globulin, albumin/globulin ratio, blood urea nitrogen, creatinine, blood urea nitrogen/creatinine ratio, glucose, alanine aminotransferase, and alkaline phosphatase) and hematology (platelet count, hemoglobin, hematocrit, mean corpuscular volume, mean corpuscular hemoglobin, mean corpuscular hemoglobin count, red blood cell count, and white blood cell count with differential [lymphocytes, monocytes, neutrophils, eosinophils, and basophils]). CBC, PT, APTT, TEG (if available), blood gas analysis, blood lactate and basic biochemistry. Eligible subjects receive strontium L-lactate as an oral dosage form (e.g., solution, tablet, or capsule) that provides an effective dose of strontium. The actual dose is based upon an allometric conversion from the human dose that has been shown to be effective in previous clinical trials and the results of the bioavailability study that is completed as disclosed in Example 12. Dosing occurs once daily for a period of 12 weeks following onset of treatment. Clinic visits are scheduled for subject dogs at study initiation and at 6 and 12 weeks following the onset of treatment. Subject dog owners use an owner-assessment diary to be filled out daily for the 12-week study period and are instructed to record any changes in the overall subject health, changes in exercise routine, and any apparent discomfort associated with ingestion of treatment. Treatment compliance is checked at the final clinic visit by owner interview and by counting the number of unused doses of the study medication.

Statistical Analysis. Descriptive statistics are calculated, including mean age and weight. Post-baseline statistical analyses are performed as repeated measures analysis of variance. The items found to have statistical significance with repeated measures analysis of variance are then compared using a Wilcoxon test for dependent samples. In all cases, statistical significance is accepted at $P<0.05$. Analysis of the primary end point and all secondary end points is conducted on the intent-to-treat population (i.e., including all subjects with at least one efficacy assessment).

Expected Outcomes. Dogs receiving strontium exhibit improvement in joint function, as demonstrated by reductions in serum CTX-II and by owner and veterinary records indicating a reduction in lameness and pain, together improvements in movement and gait.

Example 14. Effect of Strontium L-Lactate on Bone Replacement

Hairline fractures, infection, dental extraction, bone metastasis, and orthopedic surgery may lead to a local loss of bone tissue. Bone defect healing occurs naturally after a phase of bleeding and inflammation and terminates with the formation of woven bone which is then remodeled by osteoclasts and replaced by lamellar bone by osteoblasts. The age of the individual, hormonal status, nutrition, and presence of concomitant diseases may negatively affect bone tissue healing and the filling of the defect. In cases of extensive bone loss requiring prosthetic fixation, as well as in fragile osteoporotic individuals, a treatment accelerating bone healing contributes to well-being and quality of life. The results of the following study are expected to confirm both the efficacy and safety of strontium L-lactate treatment of a surgically induced bone defect in an animal model.

Animals and Diet.

All experimental designs and procedures are approved by an Animal Ethics Committee. Sixty 6-month old Sprague-Dawley female rats are housed individually at 25° C. with a 12:12-h light-dark cycle and strictly pair-fed a laboratory diet containing 15% casein, 0.8% phosphorus, 1% calcium, 70-80% carbohydrate, and 5% fat. Demineralized water is available ad libitum. Rats then are divided into six groups of 10 animals each. For a period of 4, 8, and 12 weeks after surgery, three groups (one for each time point) are treated with Sr L-lactate in gelatin administered at a dose of 200 mg Sr/kg/day, 5 days/week. This dose level leads to blood strontium concentration close to the level in human blood after a therapeutic dose of 2 g/day Sr ranelate. The three control groups receive gelatin containing 0.5% carboxymethylcellulose 5 days a week for 4, 8, and 12 weeks with dosages corresponding to those administered in the Sr L-lactate-treated group.

Surgery.

Animals are anesthetized with ketamine (100 mg/kg) and xylocaine (10 mg/kg) administered as an intraperitoneal injection. Skin of both legs is shaved and cleaned with 70% ethanol. Under aseptic conditions, an anterior 10-mm incision is made to gain access to the proximal medial section of the tibia metaphysis. A standardized drill-hole defect (2.5 mm diameter, 2 mm depth, and approximately 10 $mm^3$ total volume) is created in the proximal tibia secondary spongiosa of both legs using a dental burr under saline irrigation. The proximal limit of bone defect is delimited by a virtual line perpendicular to the long axis of the tibia and crossing the anterior edge of the growth plate centrally, which is curved both anteriorly and inferiorly in this central region. A second anatomical landmark is defined by a virtual line from the inferior border of the tendinous insertion on the proximal anterior tibial crest to a medial tendinous insertion likely corresponding to the pes anserinus in humans. The bone defect is performed midway between these two tendinous insertions. Rotatory speed does exceed 2000 rpm, and drilling is accompanied by profuse saline irrigation to avoid thermal bone necrosis. After creation of the bone defect, the skin is sutured using a 3-0 resorbable suture. Blood is sampled before surgery and at the moment of sacrifice from the tip of the tail and the aorta, respectively. At the end of the experiments, all rats are sacrificed by an overdose of ketamine hydrochloride.

Microcomputerized Tomography ($\mu$Ct).

Tibias are carefully excised immediately after death and frozen at $-20°$ C. in plastic bags. Bones are thawed slowly at $4°$ C. and maintained at room temperature the night before $\mu$Ct analysis. Each proximal tibia is secured in a cylindrical sample holder in NaCl solution and then scanned using $\mu$Ct. Three-dimensional images of each tibia are acquired with a voxel size of 20 $\mu$m in all spatial directions. The resulting gray-scale images are segmented using a low-pass filter to remove noise and a fixed threshold to extract the mineralized bone phase. Trabecular bone is analyzed by setting the volume of interest (VOI) as a circular band of 2.5 mm drawn on a slice-based method, starting from the first slice from the external bone surface containing no cortical bone and moving 30 slices dorsally, including avoidance of undrilled bone. Each slice is calculated directly from the binarized VOI. Total volume (TV) is calculated as the volume of the whole sample examined.

Bone volume (BV) is calculated using tetrahedrons corresponding to the enclosed volume of the triangulated surface. Mean trabecular thickness (Tb.Th) is determined from the local thickness at each voxel representing bone. Trabecular number (Tb.N) is calculated by taking the inverse of the mean distance between the middle axis of the structure and trabecular separation (Tb.Sp) by applying the technique used for the direct thickness calculation to the non-bone parts of the 3D image. Connectivity density based on Euler number (Conn. D) and the structure model index (SMI) is calculated. BV/TV, Tb.Th, Tb.N, Tb.Sp, and SMI are analyzed within a subregion of trabecular bone bordering the defect enclosed in a circular stripe of 0.45 mm and excluding the central cavity. Scans are successively reformatted to the axial cuts to measure the thickness of cortical bone bridging the defect. The contours of cortical bone are semi-automatically drawn within 90 slices along the long axis of the tibia, exclusively including the cortices sealing the gap.

Nanomechanical Testing.

Right tibias are embedded in polymethyl methacrylate (PMMA) and blocks are then transversally cut in two pieces at the level of the bone defect using a diamond wire saw. The face of the transverse cuts is polished and finished with 0.25 $\mu$m diamond solution. After these preparation steps, specimens are frozen at $-20°$ C. The night before the nanomechanical test, specimens are slowly thawed at $4°$ C., maintained at room temperature, and immersed in saline solution during the whole analysis.

Nanoindentation is performed using a nanohardness tester. In this test, force-displacement of a pyramidal diamond indenter that is pushed onto the bone is recorded. The nanoindentation tests include five indents within the bone defect and five indents at the junction between old and new formed bone in cortical bone. All the indents are performed at distance of the junction of the PMMA and bone. Indents are made up to 900 nm maximum depth applying an approximate strain rate of 0.0661/s for both loading and unloading. At maximum load, a 5-s holding period is applied, and the limit of the maximum allowable thermal drift is set to 0.1 nm/s.

Wavelength X-Ray Dispersive Spectroscopy (WDS).

WDS is performed to evaluate the surface distribution of Sr, Ca, and P in the bone of five representative samples from the Sr-treated and vehicle group (12 weeks of treatment only). Semiquantitative analyses are performed in profiles selected in trabecular bone at the edge with the defect in two representative samples for each treatment group (vehicle and Sr) using an X-ray spectrometer. The bone samples utilized are embedded in PMMA and cut transversally in the middle, across the defect. The surface is polished, finishing with 0.25 $\mu$m diamond solution, and coated with carbon to render them conductors and to avoid surface charging.

Statistical Analysis.

All results are expressed as means±SEM. For normally distributed data, significant differences are identified by analysis of variance (ANOVA) and Fisher's post hoc test.

Expected Results.

After 4 weeks of Sr L-lactate treatment, cortical bone thickness is significantly higher than that of time-matched vehicle controls. $\mu$CT analysis shows that the cortical bone healing area over the defect is almost completely restored in Sr-treated rats at this time. Most parameters of bone microarchitecture, such as BV/TV, Conn.D, and Tb.Th, are higher after 4 weeks of Sr treatment compared to the controls. A consistently higher trabecular BV/TV is observed at 4 weeks and this difference becomes significant after 8 and 12 weeks of Sr treatment when compared to the time-matched controls. Tb.Th follows the same trend as BV/TV at 4, 8, or 12 weeks of treatment. A higher Conn.D is observed after 4 weeks of Sr treatment and an even larger difference is observed after 8 and 12 weeks when compared to vehicle-treated rats. When analyzing trabecular bone by $\mu$CT within a circular band of 0.45 mm at the periphery of the defect and omitting the central part of the cavity, the average BV/TV values measured in Sr-treated exceed about 20%. These values are expected to be higher than BV/TV measured in the secondary spongiosa of proximal tibiae in intact (untreated) rats of the same age and strain. By 12 weeks, higher BV/TV in this region is associated with significantly higher Tb.N. and Tb.Th and lower Tb.Sp and SMI versus controls.

By 4 weeks of Sr treatment, a higher elastic modulus, hardness, and working energy of cortical bone bridging the defect is observed when compared to vehicle-treated rats. Working energy is also higher after 8 weeks of Sr treatment, although values by week 12 these parameters are comparable to those observed in time-matched vehicles. By weeks 8 and 12, elastic modulus and hardness of cortical bone are higher both in Sr- and vehicle-treated groups.

Wavelength X-ray suggests that Sr administration improves the structure of bone healing the defect versus normal, undamaged bone. In addition, Sr administration for a longer period of time further improves the microarchitecture of bone extending through the central cavity from the periphery of the defect. It is known that the Sr-dependent increase in bone strength relies on the sum of positive effects on both microarchitecture and material properties as shown by a finite element analysis.

Nanoindentation analysis shows a clear effect of Sr on material level properties of both cortical and trabecular bone repairing the defect when compared to vehicle-treated rats. Increases in elastic modulus, hardness, and working energy are observed after 4 weeks of Sr administration versus time-matched vehicle animals in both cortical and trabecular bone, healing the defect. Sr L-lactate administration also improves bone strength by increasing the elastic modulus, hardness, and working energy in rat vertebrae (i.e., sites remote from the original site of bone defect).

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

When introducing elements of the present application or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

Without further elaboration, it is believed that one skilled in the art can, using the preceding description, utilize the present application to its fullest extent. The specific embodiments are, therefore, to be construed as merely illustrative, and not limitative of the remainder of the disclosure in any way whatsoever. While the present application has been described in some detail for purposes of clarity and understanding, one will appreciate that various changes in form and detail can be made without departing from the true scope of the application.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A method of preparing a pharmaceutical quality strontium L-lactate composition comprising:
    a. selecting an L-lactic acid having at most trace concentrations of metals selected from the group consisting of aluminum, arsenic, barium, calcium, cadmium, chromium, lead, mercury, and thallium;
    b. selecting a strontium carbonate, strontium oxide, or strontium hydroxide having at most trace concentrations of metals selected from the group consisting of aluminum, arsenic, barium, calcium, cadmium, chromium, lead, mercury, and thallium;
    c. dissolving the L-lactic acid in water to obtain a homogeneous 0.1 M solution;
    d. adding portions of strontium carbonate, strontium oxide, or strontium hydroxide to the vessel containing the solution of L-lactic acid until a mass of said strontium salt equal to 0.45-0.55 mole equivalents of L-lactic acid has been added and agitating the reaction mixture until a homogeneous solution is obtained;
    e. removing particulate from the reaction mixture by filtration or centrifugation to provide a clarified solution;
    f. diluting the clarified solution with a water-miscible, aprotic organic solvent to form a precipitate; and
    g. isolating the precipitate and drying to constant mass to provide a pharmaceutical quality strontium L-lactate composition, wherein said strontium L-lactate composition is characterized in having a strontium D-lactate content of less than about 3 weight percent strontium D-lactate.

2. The method of claim 1, wherein said pharmaceutical quality strontium L-lactate composition is characterized in having a strontium D-lactate content of less than about 1 weight percent and less than 100 ppm each calcium and aluminum.

3. A method of preparation of a pharmaceutical quality strontium L-lactate composition comprising:
    a. selecting a water-soluble salt of L-lactic acid having at most trace concentrations of metals selected from the group consisting of aluminum, arsenic, barium, calcium, cadmium, chromium, lead, mercury, and thallium;
    b. selecting a water-soluble strontium salt having at most trace concentrations of metals selected from the group consisting of aluminum, arsenic, barium, calcium, cadmium, chromium, lead, mercury, and thallium;
    c. dissolving one mole equivalent of the water-soluble L-lactate in the minimum volume of water needed to obtain a homogeneous solution;
    d. dissolving 0.45-0.55 mole equivalents of the water-soluble strontium salt in the minimum volume of water needed to obtain a homogeneous solution;
    e. adding the strontium salt solution to the vessel containing the L-lactate solution and agitating until a homogeneous solution is obtained;
    f. controlling the reaction temperature, solution pH, and reaction time to ranges sufficiently low to prevent racemization;
    h. removing particulate from the reaction mixture by filtration or centrifugation to provide a clarified solution;
    i. diluting the clarified solution with a sufficient volume of a water-miscible, aprotic organic solvent to form a precipitate; and
    j. isolating the precipitate and drying to constant mass to provide a pharmaceutical quality strontium L-lactate composition, wherein said strontium L-lactate composition is characterized in having a strontium D-lactate content of less than about 3 weight percent strontium D-lactate.

4. The method of claim 3, wherein said pharmaceutical quality strontium L-lactate composition is characterized in having less than 100 ppm each calcium and aluminum.

5. A method of preparing a pharmaceutical quality strontium L-lactate composition comprising:
   a. selecting an L-lactic acid having at most trace concentrations of metals selected from the group consisting of aluminum, arsenic, barium, calcium, cadmium, chromium, lead, mercury, and thallium;
   b. selecting a strontium oxide having at most trace concentrations of metals selected from the group consisting of aluminum, arsenic, barium, calcium, cadmium, chromium, lead, mercury, and thallium;
   c. dissolving the L-lactic acid in water to obtain a homogeneous 0.1 M solution;
   d. adding portions of strontium oxide to the vessel containing the solution of L-lactic acid until a mass of strontium oxide equal to 0.45-0.55 mole equivalents of L-lactic acid has been added and agitating the reaction mixture until a homogeneous solution is obtained;
   e. controlling the reaction temperature, solution pH, and reaction time to ranges sufficiently low to prevent racemization;
   f. removing particulate from the reaction mixture by filtration or centrifugation to provide a clarified solution;
   g. diluting the clarified solution with a sufficient volume of a water-miscible, aprotic organic solvent to form a precipitate; and
   h. isolating the precipitate and drying to constant mass to provide a pharmaceutical quality strontium L-lactate composition, wherein said strontium L-lactate composition is characterized in having a strontium D-lactate content of less than about 3 weight percent strontium D-lactate.

6. A composition comprising an effective amount of a pharmaceutical quality strontium L-lactate composition wherein said pharmaceutical quality strontium L-lactate composition is characterized in having less than about 3 weight percent strontium D-lactate and less than 100 ppm each calcium and aluminum wherein the pharmaceutical quality strontium L-lactate composition is prepared by the process according to claim 1.

7. The composition of claim 6, wherein said pharmaceutical quality strontium L-lactate composition is characterized in having a strontium D-lactate content of less than about 3 weight percent.

8. The composition of claim 6, wherein said composition is characterized in containing less than 100 ppm each of metals selected from the group consisting of arsenic, barium, cadmium, chromium, lead, mercury, and thallium.

9. The composition of claim 6, wherein said composition further comprises a pharmaceutically acceptable vehicle, carrier, or diluent.

10. The composition of claim 8, wherein the composition comprises a unit dose between about 10 mg to about 300 mg strontium.

* * * * *